United States Patent
Marks et al.

(10) Patent No.: US 7,045,283 B2
(45) Date of Patent: May 16, 2006

(54) METHODS OF HIGH-THROUGHPUT SCREENING FOR INTERNALIZING ANTIBODIES

(75) Inventors: James D. Marks, Kensington, CA (US); Ulrik B. Nielson, Brookline, MA (US); Dimitri B. Kirpotin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 350 days.

(21) Appl. No.: 09/981,636

(22) Filed: Oct. 16, 2001

(65) Prior Publication Data

US 2002/0182643 A1 Dec. 5, 2002

Related U.S. Application Data

(60) Provisional application No. 60/241,279, filed on Oct. 18, 2000.

(51) Int. Cl.
*C12Q 1/00* (2006.01)
*G01N 33/53* (2006.01)
*G01N 33/566* (2006.01)
*G01N 33/573* (2006.01)

(52) U.S. Cl. ............................. 435/5; 435/4; 435/7.2; 435/7.4; 435/7.71; 435/7.72; 435/7.9

(58) Field of Classification Search .................. 435/4, 435/5, 7.1, 7.2, 7.23, 235.1, 239; 436/512; 424/130.1, 133.1, 135.1, 138.1, 155.1, 178.1; 530/300, 350, 387.1, 387.3, 387.7, 388.1, 530/388.8, 391.1, 391.3, 391.5, 391.7, 391.9
See application file for complete search history.

(56) References Cited

U.S. PATENT DOCUMENTS

| | | | |
|---|---|---|---|
| 4,885,172 A | | 12/1989 | Bally et al. |
| 5,296,348 A | * | 3/1994 | Rakowicz-Szulczynska et al. .............................. 435/6 |
| 5,389,523 A | | 2/1995 | Plant et al. |
| 5,399,331 A | | 3/1995 | Loughrey et al. |
| 5,547,669 A | | 8/1996 | Rogers et al. |
| 5,597,719 A | * | 1/1997 | Freed et al. ................. 435/194 |
| 5,770,422 A | * | 6/1998 | Collins ........................ 435/194 |
| 6,087,103 A | * | 7/2000 | Burmer .......................... 435/6 |
| 6,087,452 A | * | 7/2000 | Stewart et al. .............. 525/323 |
| 6,117,632 A | | 9/2000 | O'Mahony |
| 6,251,392 B1 | | 6/2001 | Hein et al. |
| 6,326,175 B1 | | 12/2001 | Guegler et al. |
| 6,593,308 B1 | * | 7/2003 | Szoka, Jr. ..................... 514/54 |
| 6,794,128 B1 | * | 9/2004 | Marks et al. ................... 435/5 |
| 2001/0008759 A1 | | 7/2001 | Marks et al. |
| 2002/0068272 A1 | | 6/2002 | Larocca et al. |

FOREIGN PATENT DOCUMENTS

| WO | WO 94/26787 | 11/1994 |
|---|---|---|
| WO | WO 99/10485 | 3/1999 |

OTHER PUBLICATIONS

Dietrich et al., Proceedings of the National Academy of Science, USA, vol. 92 No. 20, pp. 9014-9018 (Sep. 1995).*
Barbas et al., Proceedings of the National Academy of Science, USA, vol. 88 No. 18, pp. 7978-7982 (Sep. 1991).*
Ward et al., Journal of Immuological Methods, vol. 189 No. 1, pp. 73-82 (Jan. 1996).*
Liu et al. (1998) "Constitutive and Antibody-Induced Internalization of Prostate-Specific Membrane Antigen" *Cancer Res* 58: 4055-4060). Howe.
Tsaltas and Ford (1993) "Cell Membrane Antigen-Antibody Comples Dissiciation by the Widely Used Glycine-HCL Method: An Unreliable Procedure For Studying Antibody Internalization" *Immunol Invest*, 22: 1-12.
Matzku et al. (1990) "Antibody transport and internalization into tumours." *British Journal of Cancer*, 62(Suppl. X): -5.

* cited by examiner

*Primary Examiner*—James C. Housel
*Assistant Examiner*—Zachariah Lucas
(74) *Attorney, Agent, or Firm*—Quine Intellectual Property Law Group, P.C.; Tom Hunter; Angela P. Horne

(57) ABSTRACT

This invention provides methods of identifying ligands that are internalized into a cell. The methods typically involve i) contacting the cell with a reporter non-covalently coupled to a ligand; ii) dissociating the reporter from the ligand and removing dissociated reporter from the surface of the cell; and iii) detecting the reporter within said cell (if any is present) where the presence of the reporter within said cell indicates that the ligand binds to an internalizing receptor and is internalized.

36 Claims, 8 Drawing Sheets

```
SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: epitope tag

<400> SEQUENCE: 1

Asp Tyr Lys Asp Asp Asp Asp Lys
1               5

<210> SEQ ID NO 2
<211> LENGTH: 10
<212> TYPE: PRT
<213> ORGANISM: Artificial Sequence
<220> FEATURE:
<223> OTHER INFORMATION: His containing peptide

<400> SEQUENCE: 2

Cys Gly Gly Gly His His His His His His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: His contaiing tag

<400> SEQUENCE: 3

Cys Gly Gly Gly His His His His His His
1               5                   10
```

METHODS OF HIGH-THROUGHPUT SCREENING FOR INTERNALIZING ANTIBODIES

CROSS-REFERENCE TO RELATED APPLICATIONS

This application claims benefit of and priority to U.S. Ser. No. 60/241,279, filed on Oct. 18, 2000, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported, in part, by Department of Defense Breast Cancer Research Program Grant Nos: DAMD17-94-J-4433 and DAMD17-98-1-8189. The Government of the United States of America may have certain rights in this invention.

BACKGROUND OF THE INVENTION

With substantial completion of the first human genome sequencing project, considerable attention has turned to a determination of the biologic function of various DNA sequences. This investigation, often termed "functional genomics" represents a new phase of genome analysis. Specifically, functional genomics refers to the development and application of global (genome-wide or system-wide) experimental approaches to assess gene function by making use of the information and reagents provided by structural genomics. It is typically characterized by high throughput or large-scale experimental methodologies combined with statistical and computational analysis of the results.

One fundamental strategy in a functional genomics approach is to expand the scope of biological investigation from studying single genes or proteins to studying all genes or proteins at once in a systematic fashion. Computational biology will perform a critical and expanding role in this area: whereas structural genomics has been characterized by data management, functional genomics will be characterized by mining the data sets for particularly valuable information. Functional genomics promises to rapidly narrow the gap between sequence and function and to yield new insights into the behavior of biological systems.

One important class of genes includes those genes that encode cell surface molecules and receptors. Receptors typically bind ligands resulting in the delivery of a signal into the cell (signaling). This can lead to a number of biologic functions including, but not limited to cell growth, cell replication, cell death, etc. Other receptors mediate the specific transfer of molecules from outside the cell into the cytoplasm (endocytosis or internalization). Endocytosis is also an important mechanism by which receptor signaling is modulated. Different cell types have qualitatively and quantitatively different surface receptors and the pattern of receptor expression may change dramatically with the development and/or differentiation of a cell or tissue and/or the development and progression of a disease.

Identification of such receptors and the development of specific receptor ligands, allows the study of receptor function and the determination of the temporal-spatial pattern of receptor expression. For example, such ligands can be used to profile the pattern of receptor expression across different cell types upon exposure to a drug or during the development of a disease. In addition, cell-specific receptor ligand, more preferably internalizing cell specific receptor ligands can be used to target drugs or markers to the cell surface or into the cytoplasm (for internalizing receptors), e.g. for therapeutic effect.

SUMMARY OF THE INVENTION

This invention provides methods for identifying cell binding and internalizing ligands. Also provided are methods of identifying receptors that are capable of internalizing ligands and methods of screening for modulators of ligand internalization.

In one embodiment this invention provides a method of identifying a ligand or ligands that are internalized into a cell. The method involves i) contacting the cell with an effector (e.g. a reporter) non-covalently coupled to a ligand; ii) dissociating the reporter from the ligand and removing dissociated reporter from the surface of the cell; and iii) detecting the reporter within the cell, if the reporter is present within the cell, where the presence of the reporter within the cell indicates that the ligand binds to an internalizing receptor and is internalized. In certain embodiment the contacting comprises contacting the cell with a ligand comprising an epitope tag and contacting the cell with a reporter comprising a moiety that binds the epitope tag. In a preferred embodiment the ligand is a ligand that binds to a cell surface receptor. Preferred ligands include, but are not limited to peptides (e.g. an scFv, an Fv, an Fab, monoclonal antibody, a cytokine, a chemokine, a growth factor, etc.), nucleic acids, carbohydrates, sugars, and the like. Particularly preferred peptide ligands are produced by combinatorial chemical synthesis or recombinantly using a phage display library (e.g. using a filamentous phage).

In certain preferred embodiments, the effector (e.g. reporter) is non-covalently coupled to the ligand by an epitope tag (e.g. a His-tag, a Flag-tag, an HA-tag, a myc-tag, a DYKDDDDK (SEQ ID NO:1) epitope, etc.). Where the effector is a reporter, preferred reporters include, but are not limited to an enzyme, a colorimetric label, a fluorescent label, a luminescent label, a radioactive label, a liposome, or a liposome containing a label. In one particularly preferred embodiment the epitope tag is a hexahistidine ($His_6$) tag and said reporter is a liposome comprising a reagent that binds a $His_6$ tag (e.g. nitrilotriacetic acid (NTA)) attached to a lipid or liposome. In certain particularly preferred embodiments, the attachment is typically via a metal chelation bond, e.g. a Ni(2+) chelation bond. In another preferred embodiment the ligand is an antibody and said epitope tag is attached to the antibody through a covalent linkage to protein A.

Preferred cells for use in the methods of this invention include, but are not limited to plant cells, animal cells, and bacterial cells. Particularly preferred cells include mammalian cells, more preferably normal or pathological human cells (e.g. a cancer cell). In certain embodiments the cells are cells that overexpress one or more receptors and/or that express or overexpress a heterologous receptor.

The method can further involve isolating a ligand that is internalized into the cell. In certain embodiments, the "isolating" can comprise determining the amino acid sequence of a ligand that is internalized by the cell or determining the sequence of a nucleic acid encoding the ligand.

In another embodiment, this invention provides methods of screening a cell for internalization of a ligand. These methods preferably involve i) contacting the cell with a reporter non-covalently coupled to a ligand known to be internalizing; ii) dissociating the reporter from the ligand and removing dissociated reporter from the surface of the cell; iii) detecting the reporter within said cell, if said reporter is present within said cell, whereby the presence of the reporter within said cell indicates that said cell internalizes said ligand. Most frequently, internalization of a ligand into a cell signifies that the cell displays a receptor for the ligand that is an internalizing receptor. The method may further include isolation of the cell that internalized the ligand, e.g. from those cells that do not.

In a particularly preferred embodiment the ligand is a member of a library of ligands. Preferred libraries comprise at least 1000, more preferably at least 10,000, and most preferably at least 100,000 different members. Preferred ligands include, but are not limited to peptides (e.g. an scFv, an Fv, an Fab, monoclonal antibody, a cytokine, a chemokine, a growth factor, etc.), nucleic acids, carbohydrates, sugars, and the like. Particularly preferred peptide ligands are produced by combinatorial chemical synthesis or recombinantly using a phage display library (e.g. using a filamentous phage).

In certain preferred embodiments, the effector (e.g. reporter) is non-covalently coupled to the ligand by an epitope tag (e.g. a His-tag, a Flag-tag, an HA-tag, a myc-tag, a DYKDDDDK (SEQ ID NO:1) epitope, etc.). Where the effector is a reporter, preferred reporters include, but are not limited to an enzyme, a colorimetric label, a fluorescent label, a luminescent label, a radioactive label, a liposome, or a liposome containing a label. In one particularly preferred embodiment the epitope tag is a hexahistidine ($His_6$) tag and said reporter is a liposome comprising a reagent that binds a $His_6$ tag (e.g. nitrilotriacetic acid (NTA)) attached to a lipid or liposome. In another preferred embodiment the ligand is an antibody and said epitope tag is attached to the antibody through a covalent linkage to protein A. Particularly preferred cells are described herein.

In certain embodiments, the method further comprises isolating a ligand that is internalized into the cell. The ligand can be sequenced or the sequence of a nucleic acid encoding the ligand is determined. The method may further comprise contacting a cell with a labeled ligand again to tag or isolate the internalizing receptor.

In yet another embodiment, this invention provides methods of identifying internalizing receptors. The methods involve i) contacting a cell with a reporter non-covalently coupled to a ligand; ii) dissociating the reporter from the ligand and removing dissociated reporter from the surface of said cell; iii) detecting the reporter within said cell, if said reporter is present within said cell, whereby the presence of the reporter within said cell indicates that said ligand binds to an internalizing receptor and is internalized; iv) identifying or recovering the ligand bound to the reporter within said cell; and v) identifying a receptor that binds to the ligand. In particularly preferred embodiments, the receptor is identified by methods including, but not limited to affinity chromatography or immunohistochemistry. The method can further comprise entering the identity of the internalizing receptor into a database of internalizing receptors.

Also provided are methods of method of screening an agent for the ability to modulate internalization of a ligand into a cell. The methods preferably involve i) contacting the cell with a reporter non-covalently coupled to a ligand known to be internalized by said cell; ii) contacting the cell with a test agent; iii) dissociating the reporter from the ligand and removing dissociated reporter from the surface of the cell; and iv) detecting the reporter within the cell, if the reporter is present within the cell, where a difference in the amount of reporter internalized by the cell contacted with said test agent as compared to the amount of reporter internalized by said cell when contacted with a lower concentration of the test agent indicates that said test agent modulates the internalization of said ligand by the cell. In preferred embodiments, the lower concentration of test agent is the absence of the test agent. Preferred test agents include small organic molecules. In certain embodiments, the test agents include antibodies or peptides while in certain embodiments, the test agents do not include nucleic acids, antibodies, or peptides.

In still another embodiment, the method involves contacting the cell with a first concentration of the test agent; ii) contacting the cell with a reporter non-covalently coupled to a ligand known to internalize into the cell; iii) dissociating the reporter from the ligand and removing dissociated reporter from the surface of the cell; iv) detecting the reporter within the cell to obtain a first measurement that signifies the amount of the reporter/ligand construct internalized by the cell; v) contacting said cell with a second concentration of the test agent wherein the second concentration is higher that the first concentration; vi) repeating the steps ii)—iv) to obtain a second measurement that signifies the amount of the reporter/ligand construct internalized by the cell influenced by a second, higher concentration of the agent; and vii) comparing the first and the second measurements wherein when the first and the second measurements are different, the test agent modulates internalization of said ligand in said cell.

In certain preferred embodiments, the first, lower concentration of test agent is zero, i.e. the absence of the test agent. Preferred test agents include small organic molecules. In certain embodiments, the test agents include antibodies or peptides while, in certain embodiments, the test agents do not include nucleic acids, antibodies, or peptides.

In still another embodiment, this invention provides a construct for use in the methods of this invention (e.g. for screening a cell for an internalizing receptor). Preferred constructs comprise a ligand non-covalently coupled to an effector (e.g. a reporter) through an epitope tag. In preferred constructs the ligands include, but are not limited to peptides (e.g. an scFv, an Fv, an Fab, monoclonal antibody, a cytokine, a chemokine, a growth factor, etc.), nucleic acids, carbohydrates, sugars, and the like. Particularly preferred peptide ligands are produced by combinatorial chemical synthesis or recombinantly using a phage display library (e.g. using a filamentous phage).

In certain preferred constructs, the effector (e.g. reporter) is non-covalently coupled to the ligand by an epitope tag such as a His-tag, a Flag-tag, an HA-tag, a myc-tag, a DYKDDDDK (SEQ ID NO:1) epitope, etc. Where the effector is a reporter, preferred reporters include, but are not limited to an enzyme, a colorimetric label, a fluorescent label, a luminescent label, a radioactive label, a liposome, or a liposome containing a label. In one particularly preferred embodiment the epitope tag is a hexahistidine ($His_6$) tag and the reporter is a liposome comprising a reagent that binds a $His_6$ tag (e.g. nitrilotriacetic acid (NTA)) attached to a lipid or liposome. In another preferred embodiment the ligand is an antibody and said epitope tag is attached to the antibody through a covalent linkage to protein A. In certain preferred embodiments, the construct is polyvalent for the ligand.

This invention also provides ligand libraries for use in the methods of this invention. Preferred libraries comprise a plurality of constructs as described herein where the members of the library each comprise a ligand and an epitope tag where the ligands vary between members of the library and the epitope tags are constant among members of the library. The ligand/effector (e.g. reporter) components of the library members may be pre-assembled or may assemble during when they are combined, e.g. in the presence of a cell. Preferred libraries comprise at least $10^5$ different ligands.

In still another embodiment this invention provides a kit for screening a cell for an internalizing receptor. Preferred kits comprise a construct or a library of constructs as described herein. Preferred kits further comprise instructional materials teaching the use of said library to screen for internalizing ligands or to identify an internalizing receptor.

In yet another embodiment, the invention provides method of detecting binding and internalization of the ligands by cells. The method involves i) contacting the cell with an effector (e.g. a reporter) non-covalently coupled to a ligand; ii) removing a portion of the effector which is not associated with the cell; iii) detecting the reporter associated with the cell to obtain a first reading indicating a total amount of the ligand which is bound to the cell surface and internalized by the cell; iv) dissociating the reporter from the ligand and removing dissociated reporter from the surface of the cell; v) detecting the reporter remaining in the cell to obtain a second reading indicating an amount of the ligand which is internalized; and vi) subtracting the second reading from the first reading to obtain a difference indicating an amount of the ligand bound to cell surface. In some cases, following the contacting step it is advantageous to arrest further internalization process, for example, by reducing temperature of the cells, typically to about 4° C., or by treatment of the cells with effective amounts of metabolic inhibitors, e.g. anhydroglucose or sodium azide. In certain embodiment the contacting comprises contacting the cell with a ligand comprising an epitope tag and contacting the cell with a reporter comprising a moiety that binds the epitope tag. In a preferred embodiment the ligand is a ligand that binds to a cell surface receptor. Preferred ligands include, but are not limited to peptides (e.g. an scFv, an Fv, an Fab, monoclonal antibody, a cytokine, a chemokine, a growth factor, etc.), nucleic acids, carbohydrates, sugars, and the like. Particularly preferred peptide ligands are produced by combinatorial chemical synthesis or recombinantly using a phage display library (e.g. using a filamentous phage).

In certain preferred embodiments, the effector (e.g. reporter) is non-covalently coupled to the ligand by an epitope tag (e.g. a His-tag, a Flag-tag, an HA-tag, a myc-tag, a DYKDDDDK (SEQ ID NO:1) epitope, etc.). Where the effector is a reporter, preferred reporters include, but are not limited to an enzyme, a colorimetric label, a fluorescent label, a luminescent label, a radioactive label, a liposome, or a liposome containing a label. In one particularly preferred embodiment the epitope tag is a hexahistidine ($His_6$) tag and said reporter is a liposome comprising a reagent that binds a $His_6$ tag (e.g. nitrilotriacetic acid (NTA)) attached to a lipid or liposome, e.g. via a metal chelation bond, such as Ni(2+) chelation bond. In another preferred embodiment the ligand is an antibody and said epitope tag is attached to the antibody through a covalent linkage to protein A or protein G.

Preferred cells for use in the methods of this invention include, but are not limited to, plant cells, animal cells, and bacterial cells. Particularly preferred cells include mammalian cells, more preferably normal or pathological human cells (e.g. a cancer cell). In certain embodiments the cells are cells that overexpress one or more receptors and/or that express or overexpress a heterologous receptor.

The invention also provides for metal-chelating lipids comprising sterols and capable of forming metal chelation bond with an epitope tag, preferably, with a hexahistidine tag. More preferably, metal-chelating lipids containing cholesterol-conjugated NTA metal complex are provided.

The invention also provides for metal-chelating lipids comprising a lipid, a hydrophilic polymer, and a chelation group attached to said hydrophilic polymer Preferably, the invention provides for the poly(ethylene glycol)-lipid conjugates containing a terminally attached metal chelation group. More preferably, the conjugates comprising a poly (ethylene glycol)-lipid and a terminally attached metal chelation group capable of forming a chelation bond with an epitope tag, such as an oligohistidine tag, are provided. In a particular embodiment, poly(ethylene glycol)-lipid is poly (ethylene glycol)-conjugated DSPE, and a chelation group is NTA.

The invention also provides for compositions comprising metal chelating lipids comprising a lipid, a hydrophilic polymer, and a chelation group attached to said hydrophilic polymer and capable of forming a chelation bond with an epitope tag. The invention further provides for the methods for delivery of an effector into a cell comprising contacting the cell with (i) a metal chelating lipid comprising a lipid, a hydrophilic polymer, and a chelation group attached to said hydrophilic polymer and capable of forming a chelation bond with an epitope tag, wherein said effector is associated with said metal chelating lipid, and (ii) a ligand comprising said epitope tag wherein said cell specifically binds, and optionally, internalizes, said ligand. The composition preferably includes a liposome, which comprises said metal chelating lipid and said effector.

Definitions

The terms "polypeptide", "oligopeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Proteins also include glycoproteins (e.g. histidine-rich glycoprotein (HRG), Lewis Y antigen ($Le^y$), and the like.).

The terms "nucleic acid", or "oligonucleotide" or grammatical equivalents herein refer to at least two nucleotides covalently linked together. Nucleic acids of the present invention are single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat.

Nos. 5,386,023, 5,637,684, 5,602,240, 5,216,141 and 4,469,863; Letsinger et al. (1988) *J. Am. Chem. Soc.* 110:4470; Letsinger et al. (1994) *Nucleoside & Nucleotide* 13:1597; Chapters 2 and 3, ACS Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ACS Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$ and $V_L$-encoding sequences either joined directly or joined by a peptide-encoding linker. Huston, et al. (1988) *Proc. Nat. Acad. Sci. USA*, 85: 5879–5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No: 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323–1331).

The term "specifically binds", as used herein, when referring to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The term "ligand" refers to a molecule that is or that can be specifically bound by and/or transported by another molecule. Preferred ligands include, but are not limited to peptides, nucleic acids, carbohydrates, sugars, hormones, and the like. A ligand and a molecule that it binds form a binding pair, in which each one member is regarded as a ligand in respect to the other member. Specific examples of binding pairs include antibody/antigen, antibody/hapten, enzyme/substrate, enzyme/inhibitor, euzyme/cofactor, binding protein/substrate, carrier protein/substrate, transporter protein/substrate, lectin/carbohydrate, receptor/hormone, receptor/modulator, complementary strands of polynucleotides, protein/nucleic acid repressor(inductor), receptor/virus, etc.

The term "nanoparticle", as used herein refers to a "vehicle" capable of complexing with or containing an effector (e.g. a drug, a detectable label, a cytotoxin, etc.). A preferred nanoparticle also provides a non-covalent or cleavable covalent linkage to a ligand (direct or through a linker).

An "effector" refers to any molecule or combination of molecules whose activity it is desired to internalize into a cell. Effectors include, but are not limited to labels, cytotoxins, enzymes, growth factors, transcription factors, drugs, etc.).

A "reporter" is an effector that provides a detectable signal (e.g. is a detectable label). In certain embodiments, the reporter need not provide the detectable signal itself, but can simply provide a moiety that subsequently can bind to a detectable label.

The term "modulate" when used with reference to modulation of internalization of a ligand refers to an upregulation or downregulation of the total amount or ligand internalized and/or the rate of internalization. In certain embodiments, particularly where ligand efflux is not assayed or otherwise controlled for, modulation may occur by altering the rate of efflux of the ligand and reflect net rate or net amount of ligand incorporation by a cell.

The term "test agent" refers to any agent that is to be screened for a desired activity (e.g. the ability to modulate/alter internalization of a ligand by a cell). The "test composition" can be any molecule or mixture of molecules, optionally in a suitable carrier. The term "test cell" refers to any cell to which methods of the present invention are applied.

The term "small organic molecule" typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term "detect" refers to detection or quantitative determination.

The term "chelation bond" refers to a bond between an effector and a ligand which involves an interaction between an electron pair donor and a coordination site on a metal ion leading to an attractive force between the electron pair donor and the metal ion.

The term "liposome" refers to a nanoparticle that comprises a self-enclosed layer composed of an amphipathic lipid. The layer typically is a bilayer formed by molecules that comprise a hydrophobic portion and a hydrophilic portion wherein hydrophobic portions associate in an aqueous medium to form an internal part of the layer whereas hydrophilic portions remain in contact with the medium. The layer surrounds and encloses an interior, which may contain, wholly or partially, an aqueous phase, a solid, a gel, a gas phase, or a non-aqueous fluid. An effector, e.g. a reporter, may be contained within the interior of the liposome, in the lipid layer, or attached to the outer surface of the lipid layer.

DETAILED DESCRIPTION

Figure 1:
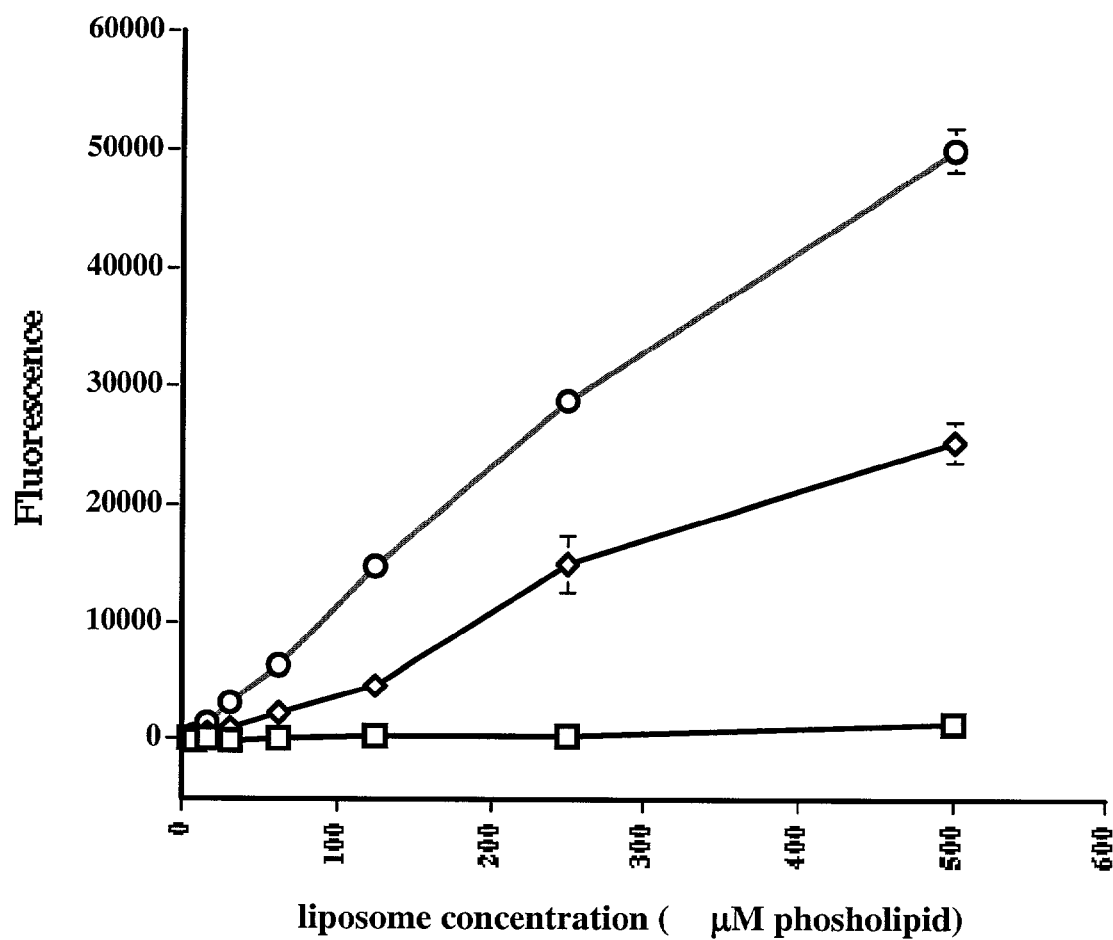
FIG. 1 illustrates the effect of Ni-NTA-lipid in the liposome on the liposome internalization into cells in the presence of a cell-internalizing ligand having a $His_6$ epitope tag. Small unilamellar liposomes containing encapsulated fluorescent marker were formulated with lipid matrix containing 0.5 mol. %, (squares), 2 mol. % (diamonds), or 5 mol. % (circles) of an NTA-lipid (DOGS-NTA-Ni, Avanti Polar Lipids, Inc., Alabaster, AL), (measured as mol. % of liposome phospholipid) and tested for internalization into ErbB2-expressing SKBR3 tumor cells using 20 μg/mL of an anti-ErbB2 scFv antibody (F5) engineered to contain a C-terminal $(His)_6$-tag. After four hours of internalization, cells were washed with physiological saline containing 1 mM EDTA, lysed in base and the fluorescence read in a microfluorimeter.

This invention provides methods of identifying ligands that are internalized into cells or to identify internalizing receptors that are capable of internalizing ligands into cells. The methods involve coupling a ligand non-covalently (e.g. via an epitope tag) to a nanoparticle containing an effector (e.g. reporter molecules, etc.) without the need for ligand purification. Since purification is not required, either before or after exposure of a test cell to the ligand coupled to the "nanoparticle", cell binding and internalization can readily be assayed in a high throughput manner.

In general, the methods involve providing an effector (e.g. reporter) non-covalently coupled to a ligand (e.g. a ligand generated in a combinatorial library). The effector/ligand is contacted with a "test" cell, e.g. a cell that is to be assayed for the ability to internalize the ligand. The effector/reporter is dissociated from the ligand and the dissociated reporter is removed from the surface of the cell. In preferred embodiments, the reporter/effector is detected within the cell and the presence of the reporter/effector within the cell indicates that the ligand is internalized. Most frequently, the internalization of a ligand signifies that the cell displays an internalizing receptor that binds the ligand. The methods can further include identifying and/or isolating the cells that internalized the ligand (and hence, the effector), for example, for a diagnostic or therapeutic purpose, wherein the cells are pathological, e.g. cancer cells, to find out if these cells are present in a tissue or fluid specimen from a patient, such as blood urine, sputum, or tissue biopsy. In another example, genetically engineered cells that express an internalizing epitope on their surface as a result of DNA transfection, can be detected and isolated. Because the surface-attached effectors are dissociated and removed under cell-sparing conditions which preserve the cell integrity, isolated cells can be maintained and propagated yielding useful clones of stable transfectants.

In another embodiment, this invention provides methods of identifying an internalizing receptor. In preferred embodiments, such methods involve identifying internalized ligands, e.g., according to the methods described above. The internalized ligands are recovered from the cell and/or identified. The recovered and/or identified ligand can then be used to identify the receptor that internalized that ligand (e.g. by labeling the receptor in situ, by affinity purifying the receptor, etc.).

In still another embodiment, the methods of this invention can be used to screen for agents that modulate the ability of a cell to internalize a ligand. In preferred embodiments, these methods entail screening for ligand internalization as described herein where the cells are contacted before or during the time they are contacted with the effector/ligand construct and) with the test agent(s) to be screened. A difference in ligand internalization by cells contacted with the test agent(s), e.g. as compared to negative controls comprising the test agent(s) at a lower concentration or the absence of the test agent(s), indicates that the test agent(s) modulate (e.g. increase or decrease) internalization the subject ligand(s).

The invention also provides the methods of detecting binding and internalization of the ligands by cells. The methods involves i) contacting the cell with an effector (e.g. a reporter) non-covalently coupled to a ligand; ii) removing a portion of the effector which is not associated with the cell; iii) detecting the reporter associated with the cell to obtain a first measurement indicating a total amount of the ligand which is bound to the cell surface and internalized by the cell; iv) dissociating the reporter from the ligand and removing dissociated reporter from the surface of the cell; v) detecting the reporter remaining in the cell to obtain a second measurement indicating an amount of the ligand which is internalized; and vi) subtracting the second measurement from the first measurement to obtain a difference indicating an amount of the ligand bound to cell surface.

Providing an Effector Non-covalently Coupled to a Ligand

In a preferred embodiment, the methods of this invention utilize an effector (typically complexed with or localized in a "nanoparticle") non-covalently attached to a ligand. In certain embodiments, an effector can be attached to a ligand by a cleavable covalent bond.

Ligands for Coupling to an Effector

Virtually any ligand is suitable for used in the methods of this invention. While, in particularly preferred embodiments, the methods of this invention utilize peptides, it is also possible to use nucleic acids, sugars, various carbohydrates, lipids, and any of a variety of organic molecules as ligands.

In certain embodiments, a single ligand can be used to identify cells and/or receptors capable of internalizing that ligand. In other embodiments, multiple ligands can be used to identify internalizing receptors and/or ligands that can be internalized by a particular cell. In particularly preferred embodiments, the ligands are provided as components of libraries comprising large numbers of different ligands, sometimes referred to as combinatorial libraries. Use of large ligand libraries comprising numerous different ligands increases the likelihood of identifying a ligand that is internalized by a particular cell.

Preferred libraries include at least 2, preferably at least 5, more preferably at least 10, and most preferably at least 100, or at least 1000 different ligands. Even larger libraries ar, possible and often preferred. Such larger libraries include at least 10,000 different ligands, preferably at least 100,000 different ligands, or even at least about 1,000,000 or more ligands.

Methods of producing combinatorial peptide libraries are well known to those of skill in the art. Such peptide libraries can be chemically synthesized or produced by expressing libraries of nucleic acids. The initial work in combinatorial library construction focused on chemical peptide synthesis. Furka et al. (1991) *Int. J. Peptide Protein Res.* 37:487–493; Houghton et al. (1985) *Proc. Natl. Acad. Sci. USA* 82: 5131–5135; Geysen et al. (1984) *Proc. Natl. Acad. Sci. USA* 81:3998–4002; and Fodor et al. (1991) *Science* 251:767.

Methods of generating peptide libraries using recombinant DNA techniques, however, are becoming quite common. Thus, for example, the use of phage display libraries and the like permit the generation of single chain antibody or other peptide ligand libraries. To express such large libraries a polypeptide or an antibody fragment gene is inserted into the gene encoding a phage surface protein (pIII) and the polypeptide-pIII fusion protein is displayed on the phage surface (McCafferty et al. (1990) *Nature,* 348: 552–554; Hoogenboom et al. (1991) *Nucleic Acids Res.* 19: 4133–4137). The gene can include an enzyme cleavage site permitting separation of the peptide from the pim protein as desired.

The nucleic acid(s) encoding the protein can be highly degenerate in one or more regions thereby providing a library of literally thousands of peptides. (see, e.g., U.S. Pat. Nos. 5,198,346, 5,096,815, 4,946,778, etc.). Libraries have been constructed comprising over 100,000 or even over 1,000,000 different members (see, e.g., Yang and Craik (1998) *J. Mol. Biol.*, 279: 1001–1011).

Phage-display methods are not the only approach to the generation of peptide libraries. To the contrary, it is possible to generate large peptide libraries using vectors other than phage.

While in certain embodiments, the ligands utilized in this invention are "randomly" generated, in embodiments, can involve building variation around a peptide "lead." In this approach, one starts with a particular peptide sequence, the lead, which may have been selected by some other random peptide approach, such as the peptides on phage approach, discussed above. One then synthesizes in vitro (e.g., with an automated DNA synthesizer) a family of oligonucleotides that is based on the coding sequence of the lead peptide. Each member of the family varies to a particular degree from the original sequence. Sources of leads include (1) quasi-random peptides generated, e.g. in phage display libraries (2) small peptide encoding DNAs derived from the genes for the natural ligands; (3) shuffling of small peptide-encoding fragments to introduce variation (see, e.g., U.S. Pat. Nos: 6,132,970, 6,117,679, 6,096,548); (4) peptide leads from other sources of peptide diversity and characterization that involve the intracellular generation of peptide diversity and detection of peptide-protein interactions via the reconstitution of a viable transcriptional transactivator (see, Field and Song, (1989) *Nature* 340(6230): 245–246); and (6) diverse peptides built around a specific conformationally constrained molecular scaffold (see, e.g., Yang and Craik (1998) *J. Mol. Biol.*, 279: 1001–1011.

Yet another approach for diversifying a selected random peptide vector involves the mutagenesis of a pool, or subset, of recovered vectors. Recombinant host cells transformed with vectors identified by screening are pooled and isolated. The vector DNA, or a portion of the vector DNA, is mutagenized by treating the cells with, e.g., nitrous acid, formic acid, hydrazine, or by use of a mutator strain such as mutD5 (see, e.g., Schaaper (1988) *Proc. Natl. Acad. Sci., USA*, 85: 8126–8130). These treatments produce a variety of mutations in the vector DNA. The segment containing the sequence encoding the variable peptide can optionally be isolated by cutting with restriction nuclease(s) specific for sites flanking the variable region and then recloned into undamaged vector DNA. Alternatively, the mutagenized vectors can be used without recloning of the mutagenized random peptide coding sequence.

One can also diversify a selected peptide by misincorporation of nucleotide changes in the coding sequence for the peptide with the polymerase chain reaction (PCR; see U.S. Pat. Nos. 4,683,202; 4,683,195; and 4,965,188) under low fidelity conditions. A protocol described in Leung et al. (1989) *Technique* 1: 11–15, utilizes altered ratios of nucleotides and the addition of manganese ions to produce a significant mutation frequency.

One can also use extensive mutagenesis to generate a large number of peptides with a significant number of differences from the lead (as well as generating peptides with few or no differences from the lead). In another approach, single amino acid substitutions in the peptide are favored, and the goal is to find a number of single amino acid differences that either abolish or significantly improve binding. For example, one approach involves the synthesis of four mixtures of nucleotides—each containing one of the four nucleotides at 85%, and each of the other three nucleotides at 5% each. Thus, at each position during solid phase chemical synthesis there is an 85% chance that the "correct" nucleotide will be incorporated and a 15% chance that one of the other three nucleotides will be incorporated (a 5% chance for each). Thus, on average, if one synthesizes an oligonucleotide 100 bases long, then in an average molecule 85% of the nucleotide positions will be correct (that is, will match the lead sequence), and 15% of the positions will have incorporated an incorrect nucleotide compared to the original sequence. Depending on the misincorporation criteria that are selected, the resulting mixture of different oligonucleotides can be quite similar to the core starting sequence, for example by following a 97%1%/1% misincorporation strategy, or quite diverged, on average, from the lead sequence, for example by following a 55%/15%/15%/15% strategy.

The approaches described above are merely illustrative. Other approaches to the generation of peptide libraries are well known to those of skill in the art (see, e.g. U.S. Pat. No. 5,010,175, Furka (1991) *Int. J. Pept. Prot. Res.*, 37: 487–493, Houghton et al. (1991) *Nature*, 354: 84–88, and the like).

The ligands used in the methods of this invention are not limited to peptide ligands. Virtually any ligand can be utilized as long as it is capable of non-covalently associating the effector/reporter. Moreover, it is possible to derivatize ligands, e.g. with a particular peptide epitope so that the ligand can non-covalently associate with a particular effector/reporter. Suitable non-peptide ligands include, but are not limited to nucleic acids (RNAs, or DNAs, or analogues thereof), sugars, carbohydrates, lipids, small organic molecules and the like.

The scope of combinatorial chemistry libraries has been expanded beyond peptide synthesis. Polycarbamate and N-substituted glycine libraries have been synthesized to produce libraries containing chemical entities that are similar to peptides in structure, but possess enhanced proteolytic stability, absorption and pharmacokinetic properties. Cho et al. (1993) *Science* 261:1303–1305; Simon et al. (1992) *Proc. Natl. Acad. Sci., USA,* 89:9367–9371. Furthermore, benzodiazepine, pyrrolidine, and diketopiperazine libraries have been synthesized, expanding combinatorial chemistry to include heterocyclic entities. Bunin et al. (1992) *J. Am. Chem. Soc.* 114: 10997–10998; Murphy et al. (1995) *J. Am. Chem. Soc.* 117: 7029–7030; and Gordon et al. (1995) *Biorg. Medicinal Chem. Lett.* 5:47–50.

Methods of chemical and/or biological synthesis, by combining a number of chemical "building blocks", as reagents can produce libraries of enormous complexity and diversity. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Known combinatorial chemical libraries include, but are not limited to,: peptoids (PCT Publication No WO 91/19735, Dec. 26, 1991), random bio-oligomers (PCT Publication WO 92/00091, Jan. 6, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261: 1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology*, 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines 5,288, 514, pyrimidinediones (see, e.g., U.S. Pat. No. 6,025,371), and the like.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the VentureTM platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Effector/Nanovarticle Combinations

In preferred embodiments, the ligand is non-covalently coupled to an effector. The coupling can be direct or to a vehicle "carrying" the effector (e.g., a nanoparticle). As used herein an effector refers to any molecule or combination of molecules whose activity it is desired to internalize into a cell. Effectors include, but are not limited to molecules such as labels, cytotoxins, enzymes, growth factors, transcription factors, nucleic acids, drugs, etc.). The drugs particularly suitable as effectors are cytotoxic anticancer drugs. Examples of cytotoxic anticancer drugs are anthacyclines (e.g., doxorubicin), vinca alkaloids (e.g., vincristine, vinblastin, vinorelbine), folate analogs (e.g., methotrexate, edatrexate), nucleotide analogs (e.g. arabinosylcytidine, azathymidine), platinum complexes (e.g., cisplatin, carboplatin), and alkylating agents (e.g., nitrosourea, melphalan, cyclophosphamide).

In particularly preferred embodiments, the effector comprises a detectable label. Detectable labels suitable for use in the present invention include any composition detectable by spectroscopic, photochemical, electrochemical, biochemical, immunochemical, magnetic, electrical, optical or chemical means. Useful labels in the present invention include biotin for staining with labeled streptavidin conjugate, magnetic beads (e.g., Dynabeads™), fluorescent dyes (e.g., fluorescein, Texas Red, rhodamine, green fluorescent protein, and the like, see, e.g., Haugland (1996), *Handbook of Fluorescent Probes and Research Chemicals*, 6th Edition, Molecular Probes, Eugene, Oreg. USA), radiolabels (e.g., $^3H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Detectable signals can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Other preferred labels include radioactive labels. Radioactive labels may be introduced into a nanoparticle which then is non-covalently linked to an effector. For example, the isotopes of $^{125}I$, $^{131}I$, $^{99m}Tc$, $^{67}Ga$, $^{111}In$, $^{14}C$, $^{3}H$, $^{35}C$, and $^{14}P$ are commonly used as radioactive labels. Radioactive metal ions such as for example, $^{67}Ga$, $^{111}In$, can be non-covalently linked to epitope tag in the form of a mixed chelate with IDA, NTA, and the like. Methods for detecting or a radioactive label are well known in the art.

Magnetic beads are also another preferred detectable label. A variety of magnetic beads compatible with cells is known in the art. See for example PCT patent application PCT WO 90 01,295, U.S. Pat. Nos. 4,101,435, 5,262,176, 4,698,302, 5,069,216, and Weissleder et al. Radiology, 175: 489–493, 1990. Polymer-coated biocompatible magnetic beads with increased magnetic susceptibility and submicron size are described by Kirpotin, Chan, Bunn, U.S. Pat. No. 5,411,730. The beads typically include magnetite or superparamagnetic iron oxide and have the size from 5 nm (superparamagnetic beads) to several micro-m. One or more ligands are attached to the beads by a non-covalent bond or by a cleavable, covalent bond. The art generally recognizes that magnetic beads can be conjugated to ligands, e.g. antibodies (Weissleder et al. *Radiology*, 182:381–385, 1992). After incubation with the cells, the beads which are not internalized, including surface-bound beads, are dissociated from the cells and removed, e.g. by washing. The cells that are capable of internalizing the ligand, and thus, have internalized the magnetic beads attached thereto, can be detected by magnitometry. Alternatively, the cells are separated using magnetic field, e.g. by high gradient magnetic separation (Miltenyi Biotech AG). Because of the biocompatibility of the magnetic beads, the separated, ligand-internalizing cells are viable and can be maintained alive, e.g. in cell culture, for future research or medical use.

It is appreciated that more than one kind of ligand can be non-covalently or cleavably covalently attached to the effector, e.g. reporter or nanoparticle carrying thereof, thus, the simultaneous selection and detection of cells for internalization of multiple ligand types in the same batch of the cells is possible.

In certain embodiments, the effector (e.g. reporter/label) is non-covalently linked to the ligand directly, while, in other embodiments, the effector is contained within and/or complexed with a nanoparticle and the nanoparticle is non-covalently coupled to the ligand. As used herein a nanoparticle is any "vehicle" capable of complexing with or containing the effector and providing a non-covalent linkage to the ligand.

A wide variety of materials are suitable as "nanoparticles" including, but not limited to porous microbeads (e.g. controlled pore glass), lipids and liposomes, various polymers, various dendrimers, and the like. Suitable liposomes include, but are not limited to various liposomes including, but not limited to small unilamellar vesicles, large unilamellar vesicles, and multilamellar vesicles. Various techniques for forming liposomes have been described in the literature, including but not limited to, pressure extrusion, detergent dialysis, dehydration-rehydration, reverse-phase evaporation, remote loading, sonication and other methods (see, e.g, New (1990) *Preparation of liposomes. In: R.R.C. New (ed.) Liposomes: A Practical Approach*. I.R.L. Press, Oxford, pp. 33–10413). Alternatively, the effector molecule(s) can simply be complexed with a lipid.

In still other embodiments, the effectors are combined with various polymers such as those used as drug carriers, and the like. Examples of suitable polymers include, but are not limited to polyvinylpyrrolidone, pyran copolymer, polyhydroxypropyl-methacrylamide-phenol, polyhydroxyethylaspartamidephenol, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

In still other embodiments, the effector(s) are complexed with various dendrimers. Dendrimers are three dimensional, highly ordered oligomeric and/or polymeric compounds typically formed on a core molecule or designated initiator by reiterative reaction sequences adding the oligomers and/or polymers and providing an outer surface that is positively changed. These dendrimers may be prepared as disclosed in PC/US83/02052, and U.S. Pat. Nos. 4,507,466, 4,558,120, 4,568,737, 4,587,329, 4,631,337, 4,694,064, 4,713,975, 4,737,550, 4,871,779, 4,857,599.

Typically, the dendrimer polycations comprise a core molecule upon which polymers are added. The polymers may be oligomers or polymers which comprise terminal groups typically capable of acquiring a charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dithiopyridyl, and sulfhydryl, among others. Preferred core molecules are ammonia, tris-(2-aminoethyl)amine, lysine, ornithine, pentaerythritol and ethylenediamine, among others. Combinations of these residues are also suitable as are other reactive residues.

Non-covalently Coupling the Ligand to the Effector/Nanoparticle.

In preferred embodiments, the ligand is non-covalently coupled to the effector and/or to the nanoparticle comprising the effector. Such non-covalent coupling can be by means of ionic interactions, coordination bonds, such as chelation bond, and/or hydrogen bonding, and/or hydrophobic interactions, and the like. In particularly preferred embodiments, the non-covalent coupling is by means of an epitope tag.

An epitope tag, as used herein refers to a molecule or domain of a molecule that is specifically recognized by an antibody or other binding partner. Thus, for example, in addition to epitopes recognized in epitope/antibody interactions, epitope tags also comprise "epitopes" recognized by other binding molecules (e.g. ligands bound by receptors), ligands bound by other ligands to form heterodimers or homodimers, oligo-histidine sequence having from 2 to 8 histidine residues, such as $His_6$ bound by Ni-NTA, and the like.

Epitope tags are well known to those of skill in the art. Moreover, antibodies specific to a wide variety of epitope tags are commercially available. These include but are not limited to antibodies against the DYKDDDDK (SEQ ID NO: 1) epitope, c-myc antibodies (available from Sigma, St. Louis), the HNK-1 carbohydrate epitope, the HA epitope, the HSV epitope, the $His_4$, $His_5$, and $His_6$ epitopes that are recognized by the His epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

In particularly preferred embodiments, the ligand is tagged with a hexahistidine ($His_6$) epitope tag which is bound by a Cu, Ni, Zn, or Co complex of a chelator group. Preferred chelator groups include iminodiacetic acid (IDA) and nitrilotriacetic acid (NTA) derivatives. One particularly preferred complex for binding $His_6$ tags is Ni-NTA which is readily coupled to an effector and/or to a nanoparticle comprising an effector (see, e.g., Example 1).

One important instance of an effector/nanoparticle is a liposome. A liposome may contain several hundreds or thousands of molecules of an effector (e.g. reporter) which leads to increased sensitivity of the methods taught by the present invention. Methods of making liposomes and loading them with various substances, such as effectors and, in particular, reporters, are known to those skilled in the art and described in comprehensive sources (see, e.g., *Liposome Technology*/Ed. by G.Gregoriadis, vol. I-III, CRC Press, Boca Raton, Fla. 1993; Lasic D. (1993). *Liposomes: From physics to applications*. Elsevier, Amsterdam, 575 pp). Liposomes with attached ligands are known to bind and/or to be internalized by certain cells (Park, et al. (1997) *Adv. Pharmacology*, 40:399–435). To form an effector/ligand construct of the present invention, one can use liposomes containing, for example, NTA- and IDA-conjugated lipids.

Metal chelating lipid conjugates capable of being incorporated into a lipid vesicle are generally described by Wagner, et al., U.S. Pat. No. 4,707,453. Unlike high-stability metal chelates, the present invention, in preferred embodiments, uses chelating lipid conjugates that produce metal complexes of moderate (or low) stability, and typically having fewer coordination sites than the metal, e.g. as in NTA- or IDA groups, so that the complex coordination sphere of the metal ion in the complex is incomplete, affording formation of the metal chelation bond between the metal and the epitope tag of the ligand. Such chelation bonds can be readily dissociated by the action of a commonly used, cell-sparing chelator/metal-binding agent with higher metal-binding strength, such as ethylenediamine tetraacetate (EDTA) or diethylenetriamine pentaatcetate (DTPA).

In preferred embodiments, the lipids are so conjugated as to allow formation of the metal chelation bond between hexahistidine epitope and the NTA or IDA or other chelating group. Typically, these conjugates are prepared using an intermediate, N-(5-amino-1-carboxyalkyl)-iminodiacetic acid (see, e.g., U.S. Pat. No. 5,047,513). Examples of such NTA lipids and IDA lipids, without limitation, are: N-(5-(1,2-dioleoyl-sn-glycero-3-succinylamido)-1-carboxypentyl) iminodiacetic acid (DOGS-NTA) (Avanti Polar Lipids, Inc., Ala. USA), 1-(N,N-dicarboxymethylamino)-3,6-dioxaoctyl-2,3-distearylglyceryl ether (IDA-TRIG-DSGE) (Northern Lipids, Inc., Vancouver, Canada), 1,2-di-O-hexadecyl-sn-glycero-3-(1'-(2'-(R)-hydroxy-3'-N-(5-amino-1-carboxy-pentyl)-iminodiacetic acid (DHGN) (Barklis et al., *EMBO J.*, 16:1199–1213, 1997), $N^\alpha,N^\alpha$-bis(carboxymethyl)-$N^{\epsilon-((}$1,2-dipalmitoyl-sn-glycero-3-phosphoethanolamido)-succinyl)-L-lysine (NTA-DPPE), and $N^\alpha,N^\alpha$-bis(carboxymethyl)-$N^\epsilon$-(N,N-dioctadecylamido)succinyl-L-lysine (NTA-DODA) ((Schmitt et al., *J. Amer. Chem. Soc.*, 116:8485–8491, 1994). Lipids comprising sterols, such as cholesterol linked to a metal chelation group capable of forming a chelation bond with an epitope tag, e.g. His-tag, are provided by the present invention.

Particularly preferred lipids for making liposome effectors/nanoparticles are metal-chelating lipids comprising a hydrophobic lipid portion, a hydrophilic polymer linked to said lipid portion, and a chelation group linked to said hydrophilic polymer. The hydrophobic lipid portion merges within a liposome lipid layer and acts as an "anchor" capable of keeping the metal-chelating lipid linked to the liposome during contact with a cell. Examples of such hydrophobic portion are those of the type generally employed to produce liposomes: phospholipids, such as phosphatidylethanolamine, steroids, such as cholesterol, glycolipids, sphingolipids, lind chain mono- and dialkylamines, a long chain dialkylcarboxylic acid or ester, an ester of a polyhydroxyalcohol, such as glycerol, and the like. The chelation group is preferably a group that binds to an epitope tag such as hexahistidine tag. Examples of such groups are nitrilotriacetic acid, iminodiacetic acid, and their C-substituted derivatives, in the form of the complexes with transition metal ions, such as divalent ions of Ni, Co, Cu, and Zn. A hydrophilic polymer is typically polyvinylpyrrolidone, polyvinyl alcohol, polyvinylmethylether, polyoxazoline or substituted derivative thereof, polyacrylic acid, amide, N-substituted amide, or ester thereof, polymetacrylic acid, N-substituted amide amide, or ester thereof, hydroxyalkylcellulose, poly(oxyalkylene), polyglycerol, polyglycolic acid, polylactic acid, water-soluble polysaccharide, poly (anhydroglucose), polyaspartamide, or hydrophilic peptide sequence. Lipid-hydrophilic polymer conjugates are generally known as liposome components (see, e.g., U.S. Pat. Nos. 5,631,018, 5,395,619, 5,013,556, 4,534,899).

The polymer typically has molecular weight from about 400 to about 2,000,000 Dalton. The molecular weight range of the suitable polymer depends on the molecular weight of a monomeric unit that composes the polymer, so that the polymer would contain more than three, preferably more than four, and most preferably at least six monomeric units. Without being bound by a particular theory, we assume that for a free motion of the polymer chain, advantageous for the unhindered access of the chelation group for the epitope tag, the chain length of the polymer would typically be equal or exceeding the length of a kinematic segment which for a flexible hydrophilic polymer typically includes 4–6 monomeric units or more. The metal chelation group is preferably a group that binds to an epitope tag such as hexahistidine tag. Examples of such groups are nitrilotriacetic acid, iminodiacetic acid, and their C-substituted derivatives, in the form of the complexes with transition metal ions, such as divalent ions of Ni, Co, Cu, and Zn. To prepare such lipid-polymer-chelation group conjugates, one may start with a lipid-polymer wherein one or more links that forms the polymer chain bear reactive chemical groups, such as, for example, carboxylic acid, carboxylic acid active ester, e.g. N-hydroxysuccinimide ester, mixed anhydride, isothiocyanate, amine, thiol, haloid alkyl, alpha-haloidalkanoyl, cyanuric chloride, N-maleimidyl, carbonyl, hyrdazido, azido, or hydroxylamino group. Such reactive groups are known to those skilled in the art (see, e.g., Hermanson (1996). *Bioconjugate Techniques*. Academic Press, New York, 785 pp.). In preferred embodiments, the chelation group is be attached using a nitrilotriacetic group having a functionalized alkyl substitute at one of the methylene groups (see, e.g., U.S. Pat. No. 5,047,513). The functionalized substitute is typically $(C_2-C_6)$-alkyl, having a functional group that reacts with the reactive group of the polymer, such as amino, thiol, or hydroxy group. Methods of making NTA-functionalized polymers are disclosed e.g. by Seed, et. al., PCT Appl. PCTIUS97/18104, WO 98/15293. Iminodiacetic acid group is attached, e.g., by conjugation of one of the carboxyl groups of a nitrilotriacetic acid to an amine or hydroxyl group in the polymer, or by the reaction between an amino group of the polymer and bromoacetic acid in an alkaline medium. In one embodiment the invention provides for the poly(ethylene glycol)-lipid conjugates containing a terminally attached metal chelation group capable of forming a chelation bond with an epitope tag. Poly(ethylene glycol) with molecular weight between about 300 and about 50,000, preferably between about 500 and about 20,000, most preferably between about 1,000 and about 5,000, is suitable.

Lipids commonly used to form liposomes, such as, di($C_{10}-C_{22}$) alkyl-(or alkenyl-) phosphatidylethanolamines, di($C_{10}-C_{22}$) alkyl-(or alkenyl-)phosphatidic acids, di($C_{10}-C_{22}$) alkyl-(or alkenyl-)phosphatidyl glycerols, di($C_{10}-C_{22}$) alkyl-, alkenyl-, alkanoyl, or alkenoyl, glycerols, sphingolipids, glycophospholipids, sterols, their derivatives, as well as synthetic lipid "anchors" such as di($C_{10}-C_{22}$) alkyl-(or alkenyl-)amines or similar alkanoyl amides are suitable. Lipid-polymer-chelator conjugates are incorporated into lipid matrix of the liposome either before, or after the liposome formation (by co-incubation with pre-formed liposomes), in the amount of 0.1–50 mol % of the liposome-lipid, preferably 0.5–10 mol. %, and most preferably at 0.5–5 mol. % of the liposome lipid. In a particular embodiment, poly(ethylene glycol)-lipid is poly (ethylene glycol)-conjugated DSPE, and a chelation group is NTA.

Equipping the effector liposome with an epitope-binding, e.g. metal chelation, group in the form of a lipid-polymer-epitope binding group conjugate provides several novel and advantageous features. The polymer-attached epitope-binding group, being situated well away from the liposome surface, and due to the polymer chain flexibility, has better access to the epitope tag within a macromolecule, e.g. a recombinant protein, thereby improving sensitivity of the methods of this invention. Significantly, the lipid-polymer-NTA-Ni conjugate, being micellarly soluble in aqueous medium, could be "captured" into pre-formed liposomes pre-loaded with the effector, e.g. cytotoxin or reporter, by mere co-incubation of the liposomes and the conjugate in an aqueous buffer.

It was a surprising discovery of this invention that after co-incubation with the effector liposomes, the epitope (e.g. hexahistidine) tag-binding activity of the liposome-captured lipid-polymer-NTA-Ni$^2$, conjugate was surprisingly well preserved, as evidenced by the selective internalization of cytotoxin carried by such liposomes into the HER2-receptor-bearing cells in the presence of an anti-HER2 scFv antibody having a hexahistidine epitope tag (see Example 4 below). The liposome having an epitope-binding group attached away from its surface, e.g. via a polymer spacer, afforded co-inclusion into the liposome of a polymer-derivatized lipid which reduces liposome aggregation, reduces background (non-specific) binding of the liposomes to cells, and when applied into the body, increases the liposome longevity in circulation (U.S. Pat. No. 5,013,556), providing for better binding of the effector/ligand constructs to the "test" cells in vivo. Typically, for reducing aggregation, the amounts of the lipid-hydrophilic polymer conjugate of 0.1–0.9 mol. % of total lipid are sufficient, while for increasing circulation longevity, the concentrations of 1–20 mol. % of total lipid are needed (U.S. Pat. No. 5,013,556). The use of epitope binding group, e.g. NTA, attached to the liposome via a polymer spacer, unexpectedly resulted in a remarkably better loading of the liposome with an effector, such as cytotoxin doxorubicin, into the effector liposome (see Example 4).

In certain embodiments, the effector can be covalently coupled to the ligand providing such coupling is readily and/or specifically cleaved. Preferably the cleavage occurs under the conditions which preserve the structural integrity of a cell such as not to allow the internalized effector, e.g. reporter, to leave the cell in the course of, or as a result of, the cleavage. Such cleavable couplings are well known to those of skill in the art. For example, in one embodiment, a linker comprising a nucleic acid restriction site or a protease recognition site is readily cleaved by application of the appropriate endonuclease or protease.

Other cleavable linkers are well known to those of skill in the art (see, e.g., U.S. Pat. Nos. 4,618,492; 4,542,225, and 4,625,014). The mechanisms for release of an agent from these linker groups include, for example, irradiation of a photolabile bond and acid-catalyzed hydrolysis. Examples of cleavable linkers include, without limitation, enamine, hydrazone, oxazolidine, ketal, acetal, ortho-esters of carbonic acid, thioesters, substituted hemiesters and hemiamides of 2-alkyl or 2,3-dialkyl substituted maleic acid, and vinyl ethers that dissociate by hydrolysis in physiological aqueous solutions at pH 3–6; disulfide bonds that dissociate in the presence of thiolytic agents (cysteine, mercaptoethanol, dithiotheitol, tris-carboxymethylphosphine, and the like, typically at 0.1–10 mM concentration) in aqueous solutions under physiological conditions of pH and salinity; ester bonds that are cleaved by base-catalyzed or enzymatic hydrolysis in aqueous physiological buffers at pH 7–9, and the bonds that are cleaved by photodissociation, such as 2-nitrobenzyl derivatives (Haugland (1996). *Handbook of Fluorescent Probes and Research Chemicals*. Molecular Probes, Inc., Eugene, Oreg. 6th Ed.).

Contacting a Cell with the Ligand/effector

In preferred embodiments, one or more "test cells" (e.g., cells that are to be screened for the ability to internalize a ligand) are contacted with the effector (e.g. reporter) non-covalently coupled to a ligand. Often a cell will be contacted with a number of different ligand/effector combinations. Contacting is typically under conditions in which the cell is capable of internalizing a ligand; that is, for example, under condition where an internalizing receptor is capable of functioning. In the case of mammalian cells, incubation at the slightly elevated temperature (30–40° C.) in an aqueous solution with physiological balanced salts and cell nutrients is preferred. Typically the cell is contacted (e.g. incubated) with the ligand/effector construct in culture although such contacting can be with cells derived from an acute/fresh preparation.

While such contacting is typically accomplished ex vivo it is recognized that, in certain embodiments, the contacting can be accomplished in vivo. It is noted that U.S. Pat. No. 6,068,829 discloses methods of identifying molecules that home to a selected organ in vivo. The methods involve transfecting a living organism with a library of ligands and identifying the ligands that localize to a particular tissue. This patent thus demonstrates the feasibility of contacting a cell in vivo with a heterologous ligand.

In particularly preferred embodiments, the ligand and the effector are joined through an epitope tag. In such embodiments, formation of the non-covalent linkage (between ligand and effector) and contacting of the cell with the ligand/effector construct can be easily combined into a single procedure. By way of illustration, Example 1 describes the incubation of NTA-liposomes, i.e. liposomes having surface-attached Ni-NTA groups, (0.5–1 mM total phospholipid) were incubated for 4 hours with the cells along with a (His) $_6$-containing ligand (~20 micro-g/mL) in 100 micro-L tissue culture media supplemented with 10% FCS at 37° C. Under such conditions, the ligands formed non-covalent linkages with the effector and were internalized by the cells.

Virtually any cell can be used with the methods of this invention. Such cells include both eukaryotic and prokaryotic cells. Bacterial cells, fungal cells, algal cells, plant cells, animal cells are all well suited to the methods of this invention. In particularly preferred embodiments, the cells are vertebrate cells, more preferably mammalian cells, and most preferably human cells. The cells can be cultured ex vivo, obtained from fresh preparations, present in a tissue culture, or in a tissue in vivo. In high-throughput screening applications, cultured cells are most preferred.

Dissociating the Effector from the Ligand

In preferred methods, after the ligand/effector construct has been contacted to the cell for a time sufficient to allow ligand internalization, the effector is separated from the ligand by dissociating the non-covalent attachment. This is accomplished by any of a number of methods well known to those of skill in the art. Methods of disrupting such non-covalent attachments include but are not limited to the use of dissociating factors and/or agents, such as heat, acidity, chaotropic agents, high salt, chelating agents, and the like. Particularly preferred are cell-sparing methods where the integrity of the cell is preserved so that after the dissociation the internalized ligand and/or effector remain essentially within the cells. If an effector and a ligand are ;linked by a metal chelation bond such as between Ni-NTA group and a $His_6$-epitope tag, the dissociating agent is preferably a reagent that binds a divalent transition metal ions, for example, strong chelator such as EDTA typically at low concentration of 0.2–5 mM, a weak metal complex-forming agent, such as imidazole, at high concentration, typically 100–300 mM, or a dithiol compound such as 2,3-dimercaptosuccinate, typically at 0.2–10 mM in a neutral physiological saline buffer. By competing for binding of a metal ion, e.g. $Ni^{2+}$, with the ligand-liposome chelation bond, these dissociating agents deprive the bond of the metal ion causing the bond to break down. In one preferred embodiment, as illustrated in Example 1, cell surface-attached liposome/ligand complexes were dissociated, and the dissociated liposomes were removed by washing the cells 3–4 times with a dissociating buffer, in this case phosphate-buffered physiological saline containing 2 mM $MgCl_2$, 2 mM $CaCl_2$, and 1 mM EDTA or with 250 mM phosphate buffered imidazole (pH 7.4). Because the internalized liposome/ligand complexes were inaccessible to the dissociating buffer, the internalized liposomes remained in the cells providing the detectable signal that indicated the presence and the amount of the internalized ligand/liposome construct.

Dissociating can involve releasing an effector, e.g. a reporter, from the nanoparticle by disrupting it, so that the released effector can be washed away from the cells. If the nanoparticle is a liposome, the releasing buffer can include a liposome-destabilizing factor. Liposomes with triggered release of encapsulated agents, induced by chemical of physical factors, for example, by briefly subjecting to pH 4–6, thiolytic agents, mild heating (42–45° C.), or light, are known in the art (see, e.g., Gerasimov et al. (1995) *Vesicles*, Ch. 17, p. 679–746; Kirpotin, et al. (1996), *FEBS Lett.*, 388:115–118). When the effector is dissociated from the ligand by disrupting a nanoparticle, e.g. a liposome, the ligand may be in the form of an amphipathic conjugate, such as lipid- or lipid-hydrophilic polymer conjugate, in which case a non-covalent bond between the ligand and the effector is by hydrophobic interactions.

Cleavable, covalent attachments between the ligand and the effector can be also destroyed in a cell-sparing matter. For example, carbonylhydrazone bonds are formed between a carboxy acid hydrazide group attached to a reporter, e.g., liposome, or a magnetic nanoparticle, and a ketone or aldehyde group produced by the periodate oxidation of a N-terminal serine or treonine engineered into a recombinant protein/peptide ligand. In the acidic aqueous environment (pH 3–6), the bond is hydrolyzed to release the reporter.

Detecting the Internalized Ligand

The internalized ligand is detected according to methods well know to those of skill in the art. The ligand can be detected directly (e.g. through various purification techniques), however, in a preferred embodiment, the ligand is detected by detecting the effector molecule attached to (or associated with) the ligand. Where the effector is a reporter (detectable label), the effector is detected using methods typically used to detect a label of the same kind. Thus, where the effector is a radionuclide, detection is by methods such as scintillography, or autoradiography. Where the effector is a colorimetric tag, detection is by optical means. Where the effector is a fluorescent tag, detection is by methods such as fluorimetry, flow cytometry, or fluorescent microscopy. When the effector is a magnetic bead, detection is by magnetometry.

Where the effector is a cytotoxin, detection of internalization can involve a measurement of cell mortality. Conversely, where the effector is a growth factor or a mitogen, detection can involve detection of cell growth or proliferation.

Assays for ligand internalization are typically scored as positive where there is a detectable signal from an internalized effector, preferably as compared to a negative control. In a preferred embodiment, to score a positive result the difference between the internalized "test" assay and the (usually negative) control is statistically significant (e.g. at greater than 80%, preferably greater than about 90%, more preferably greater than about 98%, and most preferably greater than about 99% confidence level), e.g, as determined using any statistical test suited for the data set provided (e.g. t-test, analysis of variance (ANOVA), semiparametric techniques, non-parametric techniques (e.g. Wilcoxon Mann-Whitney Test, Wilcoxon Signed Ranks Test, Sign Test, Kruskal-Wallis Test, etc.). Most preferred "positive" assays show at least a 1.2 fold, preferably at least a 1.5 fold, more preferably at least a 2 fold, and most preferably at least a 4 fold or even a 10-fold difference from the negative control.

Detecting can include quantitative determination (quantification) of the internalized ligand so that more precise comparison between various ligands as to their internalizing capacity can be made. Methods for quantification of the effector molecules such as cytofectins, enzymes, fluorescent, light-absorbing, radioactive, or magnetically susceptible substances, are known in the art (see e.g. Spector, et al. *Cells. A Laboratory Manual*, vol. 1–3, Cold Spring Harbor Laboratory Press, 1998).

Identifying the Internalizing Receptor(s)

The assays described above, can also be used to identify (e.g. previously unknown) internalizing receptors. In preferred embodiments, such methods involve identifying internalized ligands according to the methods described above. The internalized ligands are recovered from the cell and/or identified. The recovered and/or identified ligand can then be used to identify the receptor that internalized that ligand.

Methods or recovering internalized ligands are well known to those of skill in the art. This can involve lysing the cell and performing standard purification methods to isolate the labeled (effector-bound) ligand. Methods of purifying molecules from cells are well known to those of skill in the art. Typical purification methods include, but are not limited to gel electrophoresis, anion exchange chromatography (e.g. Mono-Q column, Pharmacia-LKB, Piscataway, N.J., USA), or reverse phase high performance liquid chromatography (HPLC). For a review of standard techniques see, *Methods in Enzymology Volume* 182: *Guide to Protein Purification*, M. Deutscher, ed. (1990), pages 619–626.

Alternatively, after the cell is lysed, the ligand can be dissociated from the effector and the epitope tag on the ligand can then be used to recover the ligand by affinity chromatography. Thus, for example, where the ligand is affinity tagged with a $His_6$ tag, the ligand can be recovered e.g., with an Ni-NTA affinity column, Ni-NTA gel, or Ni-NTA conjugated magnetic beads (see, e.g., QIAexpress™ Detection and Assay Handbook, Qiagen).

Detecting the Cells that Internalize a Ligand

When the method of the invention is used to detect the cells that internalize a ligand, following the step of dissociating the effector, e.g. a reporter or nanoparticle, from the ligand, the presence of the effector in the cells is detected by any means known to those skilled in the art (see, e.g., "Detecting the Internalized Ligand" above). In certain preferred embodiments, the detection methods involve examination of individual cells. Examples of such methods include, in the case of a fluorescent reporter, flow cytometry and fluorescent microscopy, and the like; in the case of a radionuclide reporter, autoradiography, and the like.

Detection of the ligand internalized in the cells can involve isolating the ligand-internalizing cells from those that do not detectably internalize the ligand. Following the dissociation of the effector, e.g. a reporter or nanoparticle, from the ligand, the ligand-internalizing cells can be isolated, for example, in the case of fluorescent reporter, by fluorescence-activated cell sorting (FACS), or in the case of the reporter being a magnetic bead, by high gradient magnetic separation. The isolated cells are then examined or utilized e.g., for research, industrial, or medical purposes.

One particularly preferred embodiment of this method involves detection of malignant cells in the body tissue or fluid samples from a patient. In this case, ligands that are selectively internalized by malignant cells, are used. For example, antibodies, such as scFv, can be selected for specific internalization into malignant or other pathological cells as described herein and in the co-pending, co-owned U.S. patent application Ser. No. 09/249,529, and used according to the present invention to detect and/or select the pathological cells in the samples of a patient body tissues or fluids.

Detecting Binding and Internalization of a Ligand by the Cells

The methods of this invention also can be used for detecting both surface-binding and internalization of a ligand by a cell. In preferred embodiments, the methods can include contacting a cell with the ligand/effector (e.g. ligand/reporter) construct, removing a portion of the construct which is not associated with the cell, i.e that is neither surface-bound, nor internalized, by the cells, and detecting the reporter associated with the cell to obtain a first reading indicating a total amount of the ligand which is bound to the cell surface and internalized by the cell. The removal of the non-cell associated portion of the reporter is preferably by removal of the ligand/reporter construct achieved by washing the cell under non-dissociating conditions, such as using phosphate-buffered saline, buffered balanced salt solution (Ringer, Hanks), cell growth medium, or other physiological medium without a dissociating agent. Thus, in the absence of these agents, the cell surface-bound ligand/effector constructs will remain intact on the cell and contribute to the signal detected from the effector providing the first measurement of the total cell-associated ligand. Then the reporter is dissociated from the ligand in a surface-bound ligand/effector constructs, and dissociated effector is removed from the surface of the cell, for example, as in the case of NTA-Ni-$His_6$-linked ligand/effector, by washing the cell with a physiological buffer containing a divalent metal ion-binding agent as described herein. Then the reporter remaining in the cell is detected providing a second measurement of an amount of the ligand/effector construct that is internalized. The difference between the first measurement and the second measurement corresponds to the amount of the ligand bound to cell surface but not internalized. In some cases, before taking the first measurement it is advantageous to arrest the internalization process without disintegrating the cell. This is readily achieved by treatment of the cell with a metabolic inhibitor, such as anhydroglucose or sodium azide, or by decreasing the temperature (chilling on ice) typically to less than 10° C., typically to about 0–4° C.

Screening for Modulators of Internalization

The methods of this invention can also be used to screen for agents that modulate the internalization of a ligand or ligands. In preferred embodiments, these methods entail screening for ligand internalization as described herein where the cells are contacted before, and/or during, and/or after the time they are contacted with the effector/ligand construct with the test agent(s) to be screened. A difference in ligand internalization by cells contacted with the test agent(s), e.g. as compared to negative controls comprising the test agent(s) at a lower concentration or the absence of the test agent(s), indicates that the test agent(s) modulate (e.g. increase or decrease) internalization the subject ligand(s). An increase of internalized ligand indicates that the test agent(s) upregulate internalization, while a decrease in internalized ligand indicates that the test agent(s) down-regulate internalization.

Depending on the duration of the assay, the increase or decrease can represent an increase or decrease in total ligand internalized or in rate of internalization (i.e. amount of ligand internalized per unit time). In still other embodiments, the ligand(s) can be screened for the ability to alter the time-course of internalization.

The assays for modulator activity are typically scored as positive where there is a difference between the activity (signal) seen with the test agent present and the (usually negative) control, preferably where the difference is statistically significant (e.g. at greater than 80%, preferably greater than about 90%, more preferably greater than about 98%, and most preferably greater than about 99% confidence level). Most preferred "positive" assays show at least a 1.2 fold, preferably at least a 1.5 fold, more preferably at least a 2 fold, and most preferably at least a 4 fold or even a 10-fold difference from the negative control (experiment where the test agent is absent or present at a lower concentration).

High Throughput Screening

The methods of this invention are well suited for high throughput screening. Particularly where an epitope tag is used to link the ligand to the effector, the assays can essentially be run in a "single step" format without elaborate purification of the ligand and/or the effector. As shown in example 1 it is sufficient to combine the subject cell(s) with the ligand and the effector at once under appropriate "incubation" conditions. The ligand joins to the effector and if the cell has a corresponding internalizing receptor the ligand is internalized into the cell along with the bound effector (e.g. label).

The cells utilized in the methods of this invention need not be contacted with a ligand and/or single test agent at a time. To the contrary, to facilitate high-throughput screening, a single cell may be contacted by at least two, preferably by at least 5, more preferably by at least 10, and most preferably by at least 20, at least 50 or even at least 100 ligands or test compounds. If the cell scores positive, it can be subsequently tested with a subset of the ligands or test agents until test agents having the activity or the internalized ligands are identified.

High throughput assays for various reporter gene products are well known to those of skill in the art. For example, multi-well fluorimeters are commercially available (e.g., from Perkin-Elmer). Other high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

High throughput screens can be performed in a number of formats known to those of skill in the art. In preferred embodiments, high throughput screens utilize a microtiter plate format (e.g. a 96 well format, a 480 well format, a 960 well format, etc.).

Delivery of Effectors into Cells

In certain embodiments this invention provides a composition for delivery of an effector into a cell, which composition comprises (i) a metal-chelating lipid comprising a hydrophobic lipid portion, a hydrophilic polymer linked to said lipid portion, and a chelation group linked to said hydrophilic polymer wherein the chelation group is complexed to a metal ion and binds to an epitope tag, and (ii) a ligand comprising said epitope tag, where the epitope tag comprises a sequence of at least two neighboring histidine residues (a histidine tag), and where effector is associated with said metal-chelating lipid. The tag preferably comprises six neighboring histidine residues (hexahistidine tag). A preferred composition is one where the metal-chelating lipid and the effector are comprised in a liposome. Any effectors andlor ligands described herein are suitable. The effector is for example, a reporter, a cytotoxin, a drug, or a nucleic acid. The ligand is typically a protein, a carbohydrate, a nucleic acid, of a small organic molecule. The ligand may be natural or synthetic. Preferred protein ligands are those that comprise the antigen-binding sequences of an antibody, such as immunoglobulins and fragments thereof, both naturally and recombinantly produced, including single-chain fragments. The liposome may further comprise a lipid-polymer conjugate, particularly, a lipid-poly(ethylene glycol) conjugate. In the liposome, the metal-chelating lipid typically constitutes between 0.1 mol % and 50 mol % , preferably between 0.2 mol. % and 10 mol %. Optionally, the lipid-polymer conjugate (without the metal-chelating group) can be included to up to 20 mol % of the liposome lipid.

Databases of Internalizing Ligands and/or Internalizing Receptors

In certain embodiments, the methods of this invention further comprise listing the identified internalizing receptors in a database identifying internalizing receptors and/or listing modulators of ligand internalization in such a database. The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

Kits

In another embodiment, this invention provides kits comprising materials for the practice of the methods described herein. In one preferred embodiments the kits comprise a container containing a ligand non-covalently coupled to a effector (e.g. a reporter) through an epitope tag. The kit may comprise a "single" construct having one type of ligand or a library of constructs providing a multiplicity of different ligands. Alternatively, an effector, e.g. a reporter or nanoparticle, can be provided, along with one or more ligands, in separate containers, so that the effector/ligand construct will be formed when the effector and the ligand are combined by a user according to the provided instructions and the needs of a particular application.

The kit can optionally include other instruments and/or reagents for practice of the methods of this invention. Such reagents and instruments include, but are not limited to microtiter plates, cells, buffers, filters for detection of fluorescent labels, software for running assays on high throughput robotic systems, and the like.

In addition, the kits can include instructional materials providing general directions and/or specific protocols for the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media can include addresses to internet sites that provide such instructional materials.

EXAMPLES

The following examples are offered to illustrate, but not to limit the claimed invention.

Example 1

A novel assay for monitorinn internalization of antibodies using metal-chelating liposomes Introduction Antibodies and antibody fragments can deliver a variety of agents such as drugs, genes, toxins or radionuclides to target cells expressing the antigen. Endocytosis of the antibody fragment to the interior of the cell can in many cases increase the therapeutic effect of the therapeutic agent. A major advantage of receptor mediated endocytosis as a drug delivery route is that therapeutic agents can be delivered specifically into target cells that overexpress the receptor and thereby increase efficacy while reducing systemic toxicity. For example, anti-ErbB2 antibodies have been used to target doxorubicin containing liposomes (Park et al. (1995) *Proc. Natl. Acad. Sci., USA*, 92: 1327–1331) or Pseudomonas exotoxin (immunotoxin) into the interior of tumor cells (King et al. (1996) *Semin Cancer Biol* 7: 79–86).

The majority of antibodies generated by immunization do not bind to receptors in a manner that triggers endocytosis (Hurwitz et al. (1995) *Proc. Natl. Acad. Sci., USA*, 92: 3353–3357). Thus it is desirable to be able to screen for antibodies that can elicit the desired response. The most common method for monitoring internalization of ligands and antibodies into cells involves radiolabeling of the protein and employs a low pH buffer (usually glycine-HCl pH 2.8) in order to dissociate surface bound antibody. However, reports from several laboratories indicate that this buffer in some cases only partially dissociates antigen-antibody complexes and therefore can introduce major inaccuracies in internalization experiments (Matzku et al. (1990) *Br. J. Cancer Suppl* 10: 1–5; Tsaltas and Ford (1993) *Immunol Invest*, 22: 1–12). Alternatively, antibodies can be biotinylated with NHS-SS-biotin and incubated with live cells. Following specific reduction of biotin groups on cell surface bound antibody with reducing agent, internalization may be quantified by immunoblotting (Liu et al. (1998) *Cancer Res* 58: 4055–4060). However, the accuracy of this method also relies on complete removal of biotin from the cell surface bound antibody. Another drawback of these methods is that they rely on laborious labeling of each ligand protein allowing only a limited number of different antibodies to be screened for internalization. The direct labeling of the protein often also results in loss of binding activity of the antibody or ligand. In addition, the stringent conditions that are required to strip the cell surface in these procedures may affect cell viability.

In this example we report a novel assay for internalization termed "Chelated Ligand Internalization Assay" (CLIA). Liposomes were formulated with $Ni^{2+}$-NTA-lipids capable of binding $(His)_6$-tagged proteins. The NTA containing liposomes were loaded with fluorescent dye and mixed with a number of different (His)6 containing anti-receptor antibody fragments or intact antibody complexed to $(His)_6$-tagged Protein A. For those antibodies that bind weakly to protein A, protein G can be used instead. Internalization of the scFv/liposome/receptor complex was detected by fluorescence microscopy or fluorimetry after gentle removal of the liposomes from cell surface bound complexes using EDTA. Cellular uptake of the complex was dependent on the specificity of the scFv as well as the ability of the antibody fragment to trigger internalization requiring <50,000 receptors/cell for detection. The assay requires only minute amounts of antibody fragment and was also performed using crude, unpurified supernatants of *E coli* expressing the antibody fragment.

Methods

Liposome Preparation

Liposomes are prepared from 1-palmitoyl-2-oleoyl-phosphatidylcholine (POPC) and cholesterol (6:4 molar ratio) and varying amounts of NTA-DOGS (Avanti Lipids; 0.5–5 mol. % of POPC amount) by lipid film hydration in solution containing 35 mM 8-hydroxypyrene-1,3,5-trisulfonic acid sodium salt (HPTS) (Molecular Probes Inc., Oreg., USA), pH 7.0, adjusted to the osmolality of 280 mmol/kg with NaCl. In some cases, the liposomes were made using 1,2-distearoyl-phosphatidyicholine (DSPC) instead of POPC, and the lipophilic fluorescent labels $DiIC_{18}(3)$-DS and $DiIC1_8(5)$-DS (0.1–1 mol. % of the liposome phospholipid) were used instead of HPTS, with the same results. In these cases, hydration is at 55–60° C. in an aqueous 140 mM NaCl buffered with 5–20 mM 4-(N-2-hydroxyethyl-piperasino)ethylsulfonic acid sodium salt (HEPES) to pH 7.2–7.4. After hydration, liposomes are formed by membrane extrusion through two 0.1 μm polycarbonate membranes (Corning) as described (Kirpotin et al. (1997) *Biochemistry* 36: 66–75). Un encapsulated HPTS was then separated by gel-filtration on a cross-linked dextran beads (SEPHADEX G-25) (Pharmacia Amersham, N.J., USA) column.

ScFv Expression and Purification

The scFv's C6.5 (anti-HER2) (Schier et al. (1995) *Immunotechnology*, 1: 73–81), and F5 (anti-HER2) (PCT/US99/07395) were cloned into expression vector pUC119mycHis (Schier et al. (1995) *Immunotechnology*, 1: 73–81) and expressed in *E. coli* TG1. Briefly, 0.75 L of media (2×TY with 100 μg/mL ampicillin and 0.1% glucose) was inoculated 1/100 with an overnight culture. The culture was grown to an $A_{600}$ of 0.9 and expression was induced by the addition of isopropyl-β-D-thiogalactopyranoside (IPTG) to a final concentration of 0.5 mM. The culture was then incubated at 30° C. for an additional four hours.

Cells were harvested by centrifugation (4000×g, 20 min.) and the pellets were resuspended in periplasmic extraction buffer (PPB) (30 mM Tris, 2 mM EDTA, 20% sucrose, pH=8) containing 100 μg/mL DNase and incubated on ice for 30 min. The bacteria were pelleted by centrifugation at 5000×g for 20 min. The pellets were resuspended in osmotic shock buffer (5 mM MgSO4) and incubated for another 20 min on ice. The bacteria were pelleted (7000×g, 20 min.) and supernatants from the PBB and $MgSO_4$ fractions were combined and cleared by centrifugation at 10000 rpm for 30 min at 4° C. The resulting solution was dialyzed in PBS (two changes, 4 L PBS pH 8). All molecules were purified by immobilized metal affinity chromatography (IMAC) (Qiagen) followed by desalting on a cross-linked dextran gel exclusion PD10 column (Pharmacia Amersham, New Jersey, USA). Protein concentrations were determined spectrophotometrically from the absorbance at 280 nm ($A_{280}$ using the absorbance value of 1.4 for 1 mg/mL protein solution in a 1 cm cuvette.

For induction in microtitre plates, wells containing 150 μl of 2×TY containing 100 μg/ml ampicillin and 0.1% glucose were inoculated with an overnight culture of *E. coli* TG1 with the plasmid containing the scFv. Cultures were grown to an $A_{600}$~1, and scFv expression induced by the addition of IPTG to a final concentration of 1 mM. Bacteria were grown overnight at 30° C., the cells removed by centrifugation, and 30 μL of the supernatant containing scFv used directly in the internalization assay.

Preparation of Protein A-$(His)_6$ Conjugate

Protein A was conjugated to the $(His)_6$-containing peptide CGGGHHHHHH (SEQ ID NO:2) using the bifunctional reagent m-maleimidobenzoyl-N-hydroxysulfosuccinimide ester (Sulfo-MBS; Pierce). 2 mg of Protein A was treated with 0.2 mg Sulfo-MBS in PBS for one hour at room temperature. Unreacted Sulfo-MBS was removed by gel filtration and the protein then reacted with 0.2 mg of the $(His)_6$-containing peptide in PBS for one hour at room temperature and unreacted peptide was removed by gel-filtration.

Assay Procedure

Human breast cancer cells SKBR3, SKOV3, BT474, MCF7, MDA-MB-453, MDA-MB-468 (American Type Culture Collection, ATCC) were grown to 80–90% confluence in the media type recommended by ATCC supplemented with 10% fetal calf serum (FCS) and harvested by trypsinization using standard techniques. Cells were seeded in 96-well plates at 10,000 cells/well and incubated overnight at 37° C. The next day, NTA liposomes (0–1 mM total phospholipid) were incubated for 4 hours with the cells along with the $(His)_6$-containing ligand (20 µg/mL unless otherwise indicated) in 100 micro-L tissue culture media supplemented with 10% FCS. When supernatants of induced E. coli cultures were used in the assay, 65 µL of cell culture media containing 10% serum and NTA-liposomes were mixed with 35 µL of supernatants. To test the internalization of monoclonal antibodies, which do not contain a $(His)_6$-tag, 10 tg/hnL of Protein A-$(His)_6$ was used to complex 40 µg/nL of a recombinant, humanized anti-HER2 monoclonal IgG HERCEPTIN (Genentech, Inc. California, USA). To strip cell surface of the liposomes linked within un-internalized liposome/ligand complexes, cells were washed 3–4 times with 170 µL PBS containing 2 mM $MgCl_2$, 2 mM $CaCl_2$, and 1 mM EDTA or with 250 mM phosphate buffered imidazole (pH 7.4). Cells were lysed in 50 PL 0.01 M NaOH before reading fluorescence at 460/530 nm in a RC4 microfluorimeter (BIOTEK).

Cell Surface Binding Measurements

Cells were harvested by trypsinization using standard techniques. The F5 was incubated in triplicate with $1 \times 10^5$ cells in 96-well plates with V-shaped wells for two hours at concentrations indicated. Cell binding was performed at room temperature in PBS containing 2% FCS and 0.1% sodium azide in a total volume of 200 µL. After two washes with 200 µL PBS, bound scFv was detected by the addition of 100 µL (10 µg/mL) of FITC labeled anti-FLAG MAb M1 (Sigma). After a 30 minute incubation at room temperature, the cells were washed twice and resuspended in PBS containing 4% paraformaldehyde. Fluorescence was measured by flow cytometry in a FACSort (Becton-Dickinson) and median fluorescence (F) was calculated using Cellquest software (Becton-Dickinson) and the background fluorescence subtracted.

Results

Liposome Formulation

Figure 2:
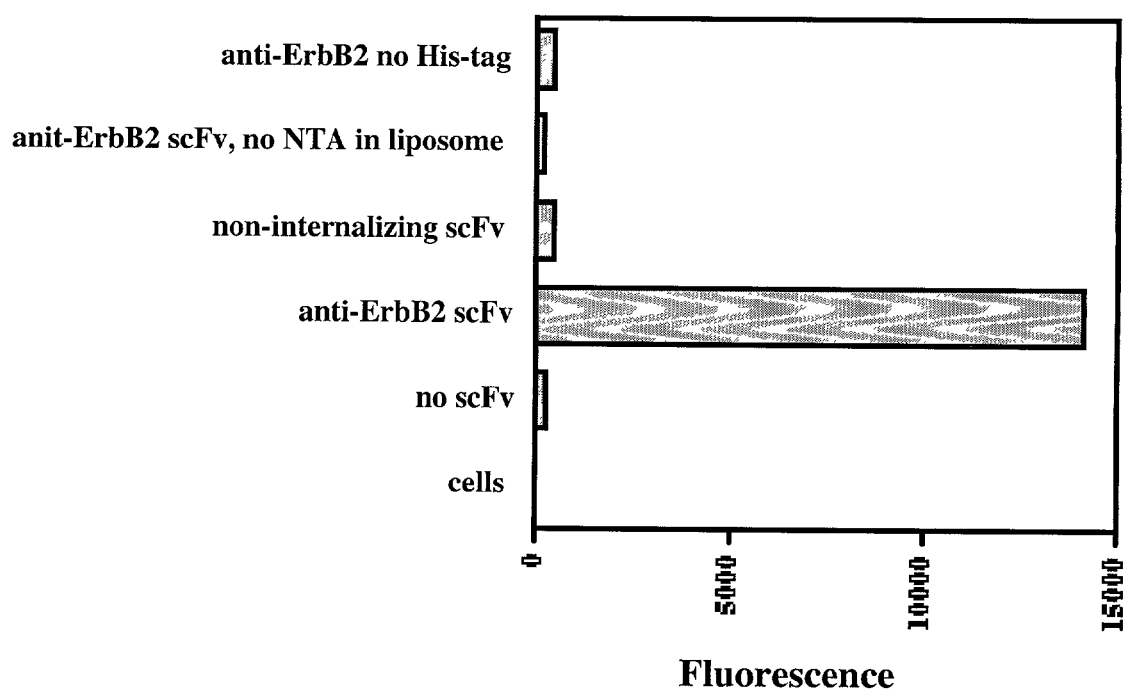
FIG. 2 illustrates the specificity of the CLIA assay. SKBR3 tumor cells were incubated with NTA-liposomes (5 mol. % Ni-NTA-DOGS) and the anti-ErbB2 antibody F5 without a $(His)_6$-tag, or a non-internalizing anti-ErbB2 antibody (C6.5), or no scFv. Alternatively, the F5 scFv containing the $(His)_6$-tag was co-incubated with fluorescently labeled liposomes formulated without the NTA-DOGS lipid. After four hours of internalization, cells were washed with physiological buffered saline containing 1 mM EDTA, lysed in base and the fluorescence read in a microfluorimeter.
Figure 3:
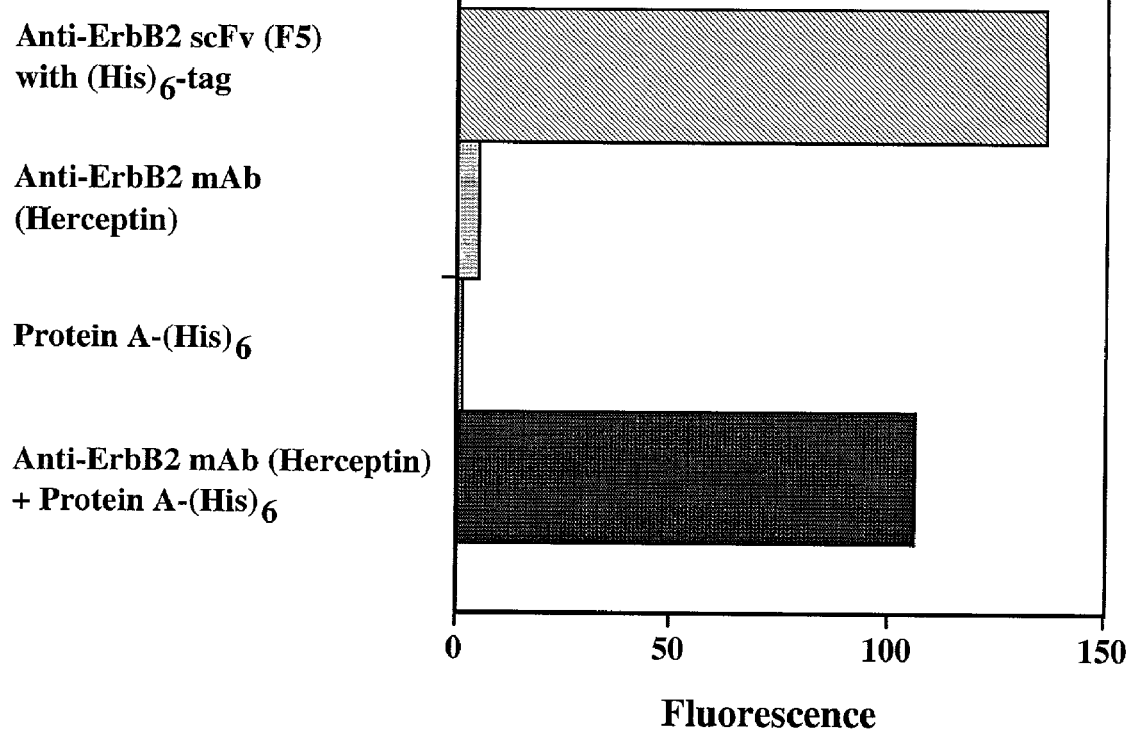
FIG. 3 illustrates monitoring of internalization monoclonal antibodies by CLIA using a Protein A-$(His)_6$ chemical conjugate. SKBR3 cells were incubated the anti-ErbB2 antibody F5 with a $(His)_6$-tag, the anti-ErbB2monoclonal antibody Herceptin, Protein A-$(His)_6$ alone, or mixture of Herceptin and Protein A-$(His)_6$. After four hours of internalization, cells were lysed in base and the fluorescence read in a microfluorimeter.

Liposomes were formulated with 0, 0.5, 2 and 5 mol. % NTA-lipid and tested for internalization into SKBR3 tumor cells using an anti-ErbB2 scFv antibody (F5) engineered to contain a C-terminal (His)6-tag. After four hours of internalization, cells were washed with 1 mM EDTA in PBS, lysed in base and the fluorescence read in a mnicrofluorimeter. The intensity of the signal increased dramatically with increasing NTA-lipid composition for the range tested (FIG. 1). The internalization was abolished when the scFv did not contain a his-tag or when liposomes were formulated without NTA containing lipid (FIG. 2). To expand the utility of the assay to full-length monoclonal antibodies, Protein A was conjugated to the peptide CGGGHHHHHH (SEQ ID NO:3) using the bi-functional reagent sulfo-MBS which cross links the thiol group in the peptide to primary amines on Protein A. SDS-PAGE analysis confirmed successful conjugation of multiple peptides per Protein A molecule as demonstrated by an apparent shift in molecular weight of approximately 10 kDa (results not shown). When SKBR3 cells were co-incubated with Protein A-$(His)_6$ and the monoclonal anti-ErbB2 antibody Herceptin, NTA-liposomes were specifically endocytosed (FIG. 2). Protein A-$(His)_6$ or Herceptin alone did not increase the uptake of NTA-liposomes, indicating that it is mediated by the Herceptin/Protein A-$(His)_6$ complex (FIG. 2).

Assay Optimization

The effect of increasing the liposome concentration in the reaction was investigated using the anti-ErbB2 scFv antibody (F5) or an irrelevant antibody binding a vascular antigen not expressed on SKBR3 cells. The cellular uptake of liposomes was proportional to the concentration of liposomes in the reaction. In the 0–800 µM phospholipid range tested, the non-specific antibody did not internalize liposomes above background (FIG. 4).

Sensitivity of the Assay

Figure 4:
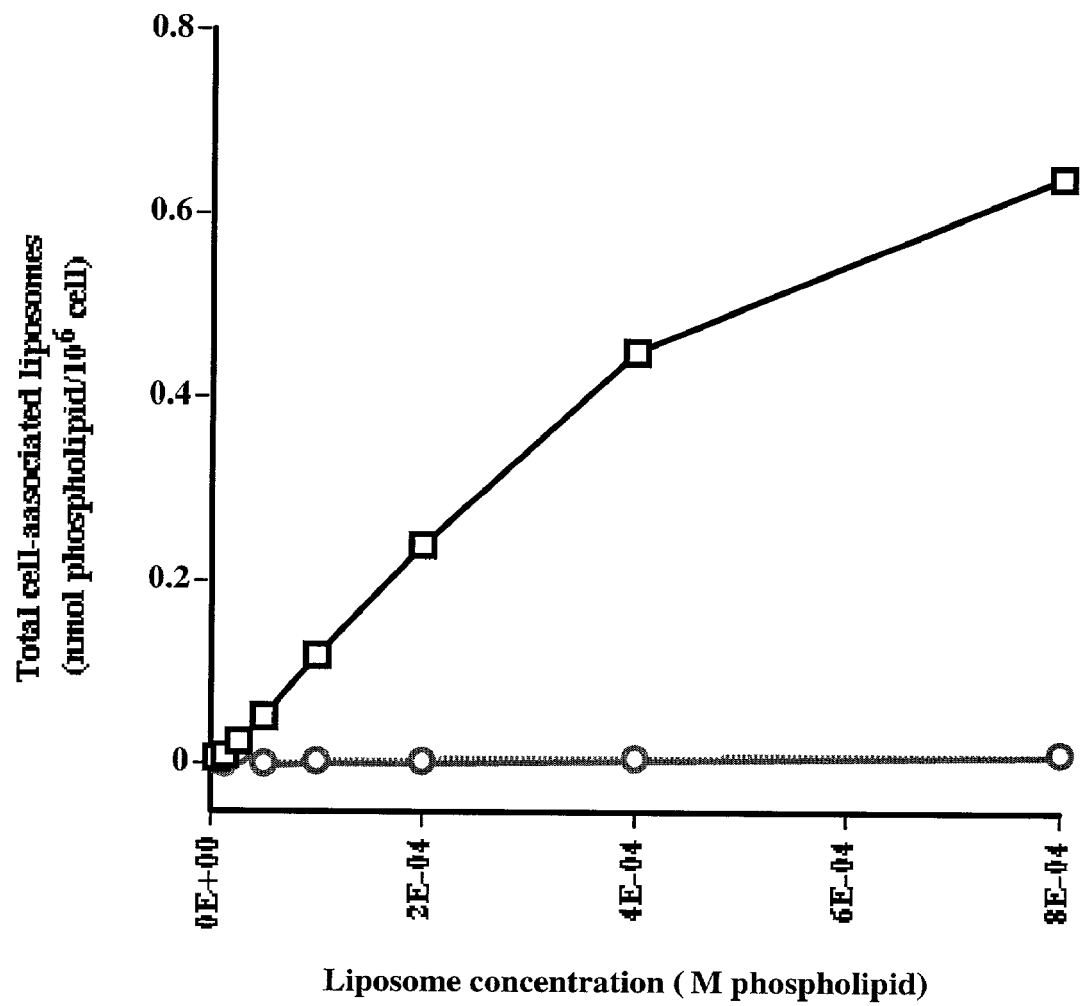
FIG. 4 illustrates the effect of liposome concentration in the CLIA assay. SKBR3 cells were co-incubated with (squares) or without (circles) 20 micro-g/mL of the anti-ErbB2 antibody F5 and varying concentrations of Ni-NTA-liposomes with encapsulated fluorescent marker. After four hours of internalization, cells were washed with physiological saline buffer containing 1 mM EDTA, lysed in base and the amount of cell-associated liposome lipid was determined from the fluorescence read in a microfluorimeter.
Figure 5:
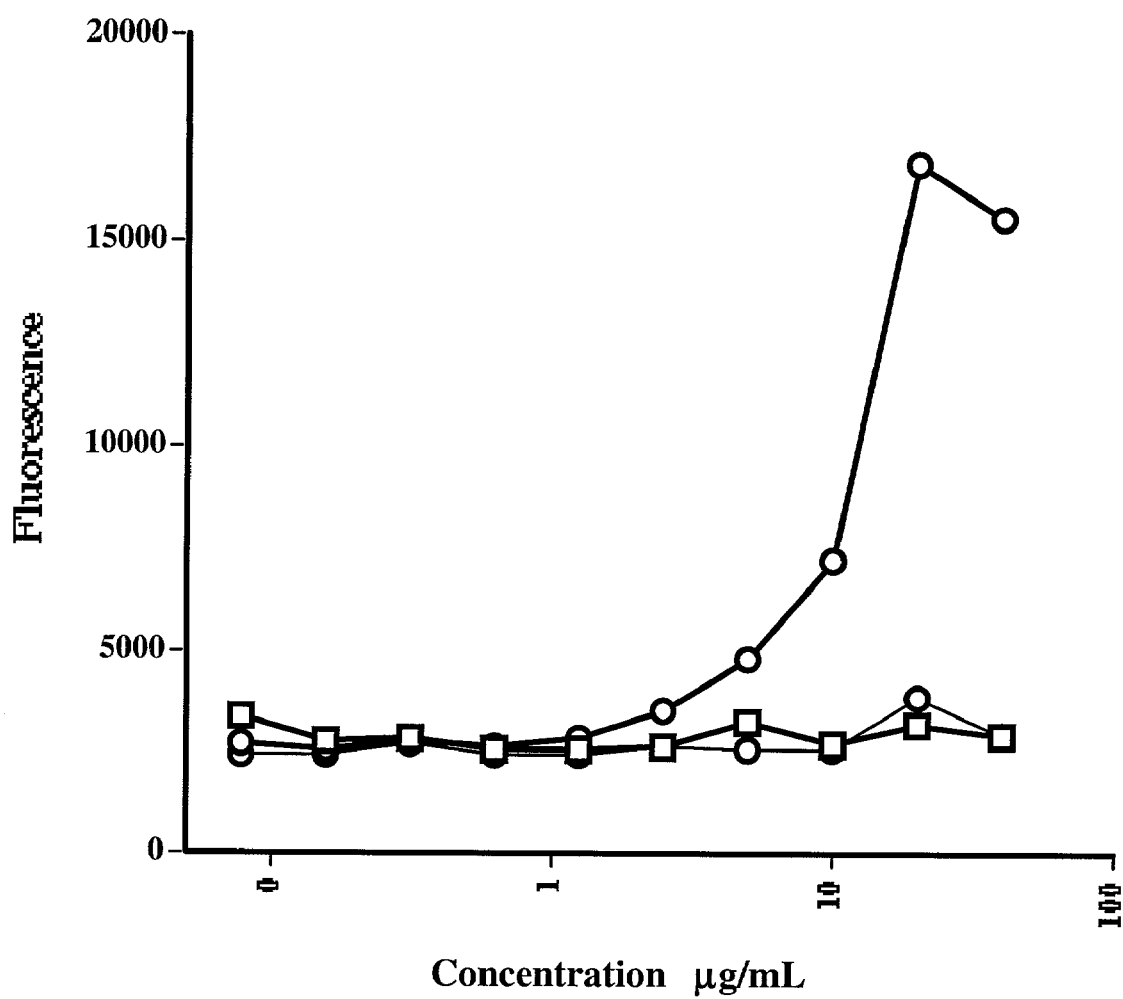
FIG. 5 illustrates the effect of antibody concentration in the CLIA assay. SKBR3 cells were co-incubated with varying concentrations of the anti-ErbB2 antibody F5 (solid line-circles), a control antibody (squares), or no antibody (dotted line—circles) and NTA-liposomes containing 2 mol. % Ni-NTA-DOGS. After four hours of internalization, cells were washed with physiological saline buffer containing 1 mM EDTA, lysed in base and the fluorescence read in a microfluorimeter.

The sensitivity of the assay was tested with varying concentrations of several antibodies to different epitopes on SKBR3 cells, FIG. 4. Only the F5 scFv antibody (anti-ErbB2) resulted in internalization of the complex. Interestingly, the irrelevant antibody (4G7) and the non-internalizing anti-ErbB2 antibody (C6.5) did not mediate internalization of the NTA-liposomes (FIG. 5). This s is consistent with previous results we obtained by confocal microscopy analysis of the internalization F5 and C6.5 The detection level of the assay with the F5 scFv on SKBR3 cells was below 1µg/mL of purified antibody.

Assay does not Require Antibody Purification

Figure 6:
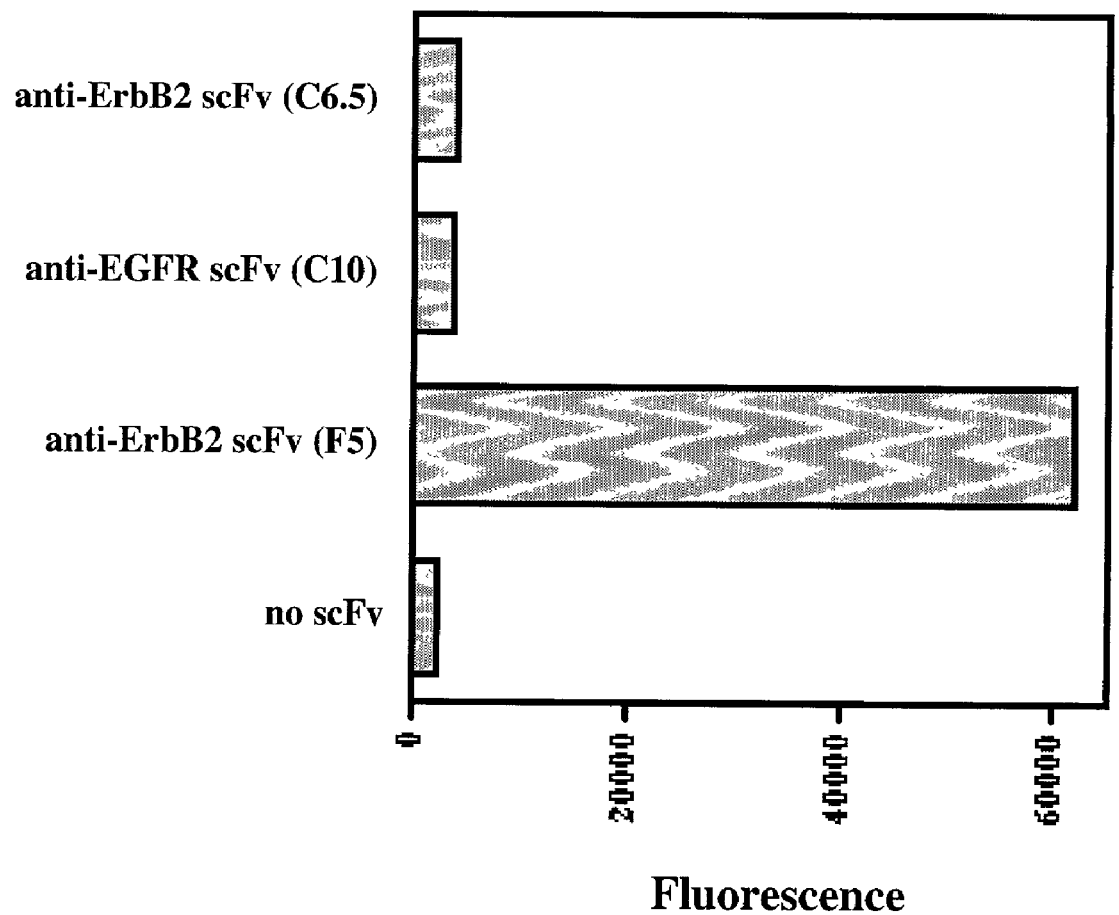
FIG. 6 shows the use of culture supernatants in the CLIA assay. SKBR3 cells were co-incubated with culture supernatants of E. coli expressing the anti-EGFR scFv antibody C10, the non-internalizing scFv antibody C6.5, the anti-ErbB2 scFv antibody F5, or no scFv along with NTA-liposomes. After four hours of internalization, cells were washed with physiological saline buffer containing 1 mM EDTA, lysed in base and the fluorescence read in a microfluorimeter.

Because of the specific interaction of the $(His)_6$-tag with NTA on the liposome, the assay should permit the use of unpurified scFv, allowing a large number of scFv molecules to be assayed for internalization. To test this, soluble scFv expression was induced from E. coli in 96-well culture plates and the supernatant tested for activity on live SKBR3 cells using 5 mol. % NTA liposomes. Previous experiments (results not shown) had determined that SKBR3 cells tolerate as much as 50% bacterial culture supernatant for up to 24 hours. Supernatants of E coli expressing the F5 scFv were mixed 1:3 with cell culture media containing 10% serum and antibiotics as well as 500 µM NTA liposomes and incubated with live SKBR3 cells. Results were similar to results obtained with 20 tg/mL of purified scFv with similar specificity (FIG. 6).

Profiling Tumor Cell Lines for Antibody Internalization

Figure 7:
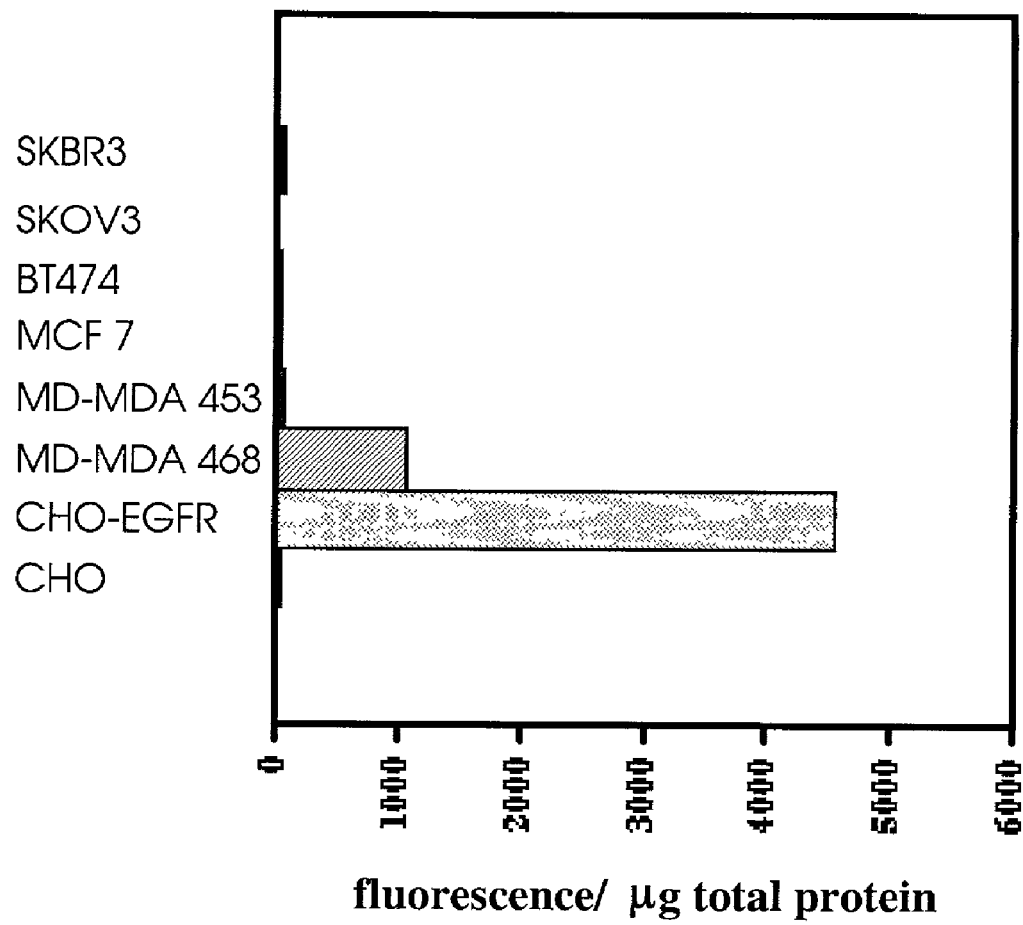
FIG. 7 illustrates tumor cell profiling with the anti-EGFR scFv antibody. The anti-EGFR antibody C10 was co-incubated with fluorescent-labeled NTA-liposomes on cell lines expressing varying amounts of EGFR: SKBR3, SKOV3, BT474, MCF7, MD-MBA 453, MD-MDA 468, CHO-EGFR, or CHO. Uptake was normalized to total cellular protein.

The scFv antibody to EGFR (C10) was used to profile a panel of breast cancer cell lines and CHO transfectants (FIG. 7). Only the cell line MD-MDA 468 and CHO cells transfected with EGFR internalized significant amounts of NTA-liposomes. The specificity of the assay is exemplified with C10 internalizing into CHO and CHO transfected with EGFR. Uptake of the fluorescent NTA liposomes into the EGFR transfected CHO cells was 165 times that of the untransfected.

Figure 8:
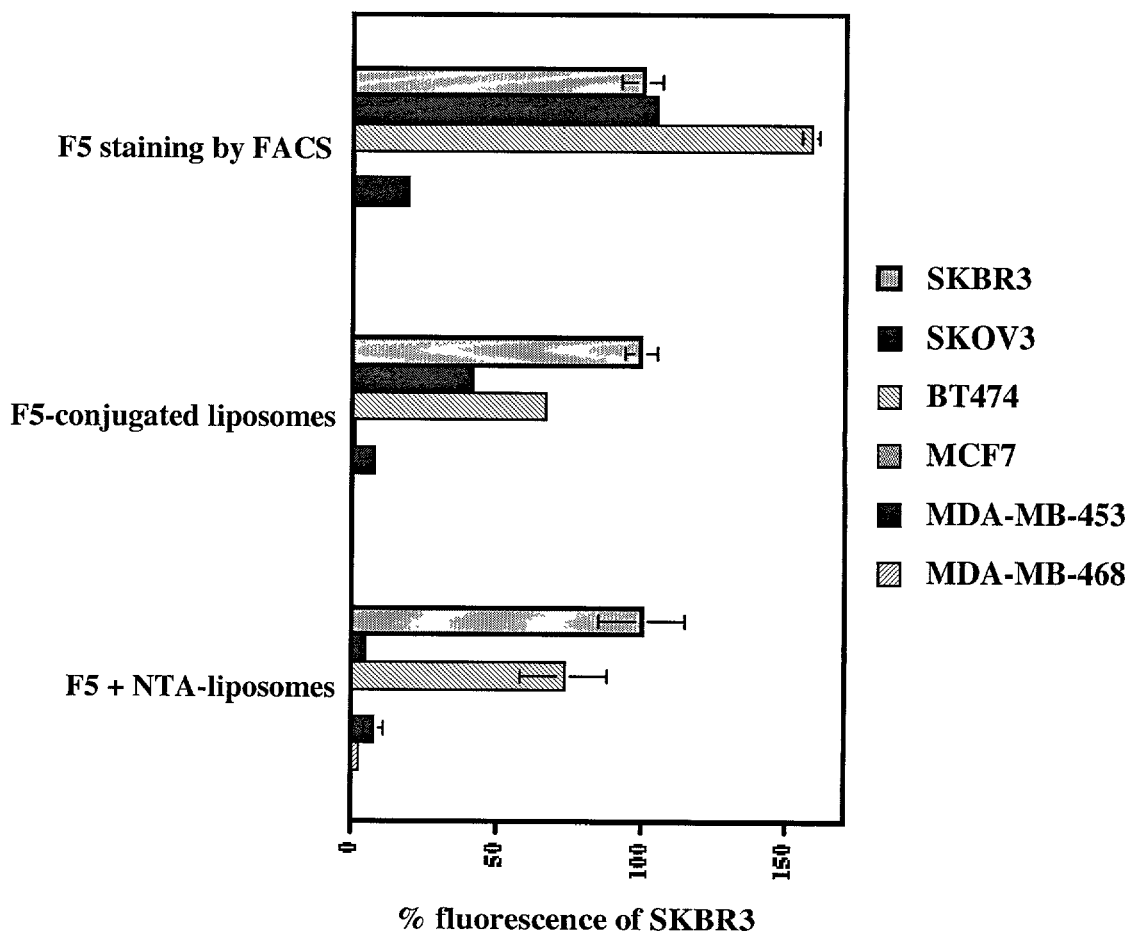
FIG. 8 shows a comparison of fluorescent anti-ErbB2 staining by flow cytometry, uptake of covalent liposomes, and the CLIA assay. Tumor cells were incubated with the anti-ErbB2 scFv F5, detected with FITC-labeled anti-FLAG antibody, and fluorescence quantified by flow cytometry. Alternatively, live tumor cells were incubated with immunoliposomes containing the F5 scFv covalently coupled to the liposome containing encapsulated fluorescent marker BPTS. The CLIA assay was performed by co-incubation of the F5 scFv and NTA-liposomes. Liposome fluorescence was read in a microfluorimeter.

The profile of F5 internalization largely correlated with cell surface expression of ErbB2 as determined by FACS with the F5 antibody (FIG. 8). However, the cell line SKOV3 did not take up as much liposome as would be expected from its cell surface expression level of ErbB2. The poor internalization of ErbB2 into this cell line has been described previously (Kirpotin et al. (1997) *Biochemistry* 36: 66–75). When total uptake into the same panel of cell lines was determined using F5-liposomes (in which the antibody is covalently coupled to the lipid via non-cleavable bond) the discrepancy with F5 scFv binding by FACS was less pronounced. This is most likely due to cell surface bound F5-liposomes, and thus when there is a covalent, non-cleavable bond between the ligand and the effector, this assay does not effectively measure internalization.

Example 2

Lipid-NTA coniugates for Epitope-mediated Non-covalent Conjugation of Ligands to Liposomes 6-(1,2-Dipalmitoylglycerol-3-succinyl)amido-2-(N,N-dicarboxymethylamino)-hexanoic acid nickel salt (DPGS-NTA-Ni).

6-amino-2-(N,N-bis-carboxymethylamno)hexanoic acid (I) was synthesized from N(epsilon)-CBZ-lysine and bromoacetic acid according to Schmitt et al. (1994), *J. Amer. Chem. Soc.* 116:8485–8491, except that removal of carbobenzoxy protecting group was in 4 M HBr/glacial acetic mixture overnight, resulting in the recovery of I as a hydrobromide.

1,2-dipalmitoyl-3-succinyl-rac-glycerol (II) was prepared from 1,2-dipalmitoyl-glycerol, succinic anhydride, and 4-pyrrolidinopyridine according to Silvius & Leventis (1987), *Biochemistry*, 26:3297.

DPG-NTA-Ni (III): 335 mg (0.5 mmol) of II was dissolved in 2.5 mL of anhydrous chloroform and 1.25 ml of anhydrous dimethoxyethane. With stirring, 66 mg (0.575 mmol) of N-hydroxysuccinimide were added, followed by the solution of 108 mg (0.525 mmol) of dicyclohexylcarbodiimide (DCC) in 0.6 ml chloroform. After 4 hour stirring at room temperature, the precipitated urea was filtered out, and the filtrate was brought to dryness under reduced pressure. The dry residue was suspended in the mixture of 1 ml chloroform and 3 ml of anhydrous methanol, and 250 mg of I hydrobromide were added, followed by 0.35 ml (5 mmol) of triethylamine. The mixture was brought to 50° C. to effect dissolution of the suspended solid, and stirred at room temperature overnight. The mixture was diluted with 10 ml chloroform and washed 3 times with 40 ml of the 50% aqueous methanol containing 0.5 M NaCl. The chloroform layer was shaken with 0.26% aqueous nickelous sulfate hexahydrate, dried over anhydrous sodium sulfate, and brought to dryness in vacuum. The dry residue was dissolved in 2 ml hexane, and filtered through GF/C grass fiber filter (Whatman). The hexane was evaporated in vacuum to yield 0.334 g (66% of theory) of the product as a greyish-blue solid, readily soluble in hexane and chloroform. TLC: Rf 0.16 (silica; $CHCl_3$-$MeOH$-$H_2O$ 65:25:4). The intended structure was confirmed by PMR.

6-(Cholesteryl-succinyl)amino-2-(N,N-bis-carboxymethylamino)-hexanoic acid nickel salt (Chol-NTA-Ni) (IV).

244 mg of cholesteryl hemisuccinate (Sigma Chemical Co., USA) were reacted with N-hydroxysuccinimide and DCC, and further with compound I hydrobromide by the same method as described for compound III. Upon addition or the nickelous sulfate solution, a greenish paste formed. The paste was extracted several times with the chloroform-methanol mixture.(5:1 by vol.). The extract was dried over anhydrous sodium sulfate, filtered through GF/C glass fiber filter, and brought to dryness in vacuum. Yield 119.5 mg (30% of theory) of a greenish solid, readily soluble in chloroform giving greenish-blue solution. TLC: Rf 0.12 (silica; $CHCl_3$-$MeOH$-$H_2O$ 65:25:4). The intended structure was confirmed by PMR.

6-(1,2-Distearoyl-sn-elycerophosphoryl-ethanolaminocarbonyl)-poly(oxyethviene)-oxycarbonvl)amino-2-(N,N-bis-carboxymethylamino)-hexanoic acid nickel salt (DSPE-PEG-NTA-Ni) (V)

198 mg (0.0445 mmol) of distearoylphosphatidylethanolaminocarbonyl-poly(ethylene glycol)-propionic acid N-hydroxysucciniinidyl ester (NHS-PEG-DSPE, Shearwater Polymers, Ala., USA) prepared from poly(ethylene glycol) with mol. weight 3,400 were dissolved in the mixture of 1 mL of anhydrous ethanol and 0.5 ml of anhydrous chloroform, mixed with the solution of 40.8 mg (0.120 mmol) of I hyrdobromide in 0.5 mL of anhydrous ethanol and 0.15 mL (1.08 mmol) of triethylamine, and stirred 2 hours at 60° C. The reaction mixture was brought to dryness and dissolved in 3 ml of 0.14 M aqueous NaCl. The mixture was clarified by centrifugation at 15,500×g for 5 mm., and clear supematant was brought to dryness in vacuum. The residue was dissolved in 2.5 ml of 0.144 M NaCl, pH was adjusted to 6.8 with 1 N NaCi, and 0.12 mL of 1 M $NiSO_4$ were added. The solution was chromatographed on a 13-mL column with cross-linked dextran beads (Sephadex G-75, Pharmacia Amersham, USA) using 0.144 M NaCl as eluent. The fractions appearing at the void volume (total 4 mL) were collected, and dried by lyophilization ovemight. The lyophilized cake was extracted with the mixture of 2 ml anhydrous ethanol and 0.2 ml chloroform; the insoluble matter was removed by centrifugation, and the clear solution was brought to dryness in vacuum. The residue was redissolved in 2 ml of ethanol containing 0.1 ml of chloroform, the solution clarified by centrifugation (15.5×g, 5 min), and brought to dryness in vacuum. Yield 92 mg (46% of theory). The bluish solid was soluble in-ift chloroform-methanol mixture (60:40 by vol.) and in water, giving light-blue solutions. The intended structure was confirmed by PMR.

Formulation into Liposomes

Compounds III, IV, V in the amount of 0.5 mol. %, 1 mol. %, 2 mol. % or 5 mol. % of the liposome lipid were formulated into small unilamellar liposomes prepared from POPC and cholesterol (3:2 molar ratio), containing fluorescent reporter HPTS, and tested in a CLIA assay using HER2-overexpressing SKBR-3 cells and a recombinant anti-HER2 scFv F5 with a hexahistidine tag as described in the Example 1 above. The results were similar to those described in Example 1 using DOGS-NTA-Ni.

Example 3

Intracellular Delivery of a Cytotoxic Liposome using Ni-NTA-PEG-DSPE and His-tagged scFv Antibody Liposomes having lipid composition of DSPC, cholesterol, methoxy-poly(ethylene glycol)-DSPE derivative (PEG(2000)-DSPE, PEG mol. weight 2,000; Avanti Polar Lipids, Ala., USA), and compound V (Ni-NTA-PEG-DSPE) in the molar ratio of 3:2:0.05:0.06 were prepared by lipid film hydration and polycarbonate track-etched membrane (0.1 jim, 10 times) extrusion at 55° C. in 0.25M aqueous ammonium sulfate. After removal of unencapsulated ammonium sulfate and bringing the liposomes into 5% dextrose, 5 mM morpholinoethanesulfonic acid (MES) buffer, pH 5.5 (adjusted with sodium hydroxide) by gel-chromatography using cross-linked dextran beads (Sephadex G-75, Pharmacia, N.J., USA), the liposomes were mixed with 10 mg/ml vinorelbine bitartrate solution USP (GlaxoWellcome, USA) to achieve drug/lipid molar ratio of 5:1 and incubated at 55° C. for 30 mm. to achieve drug encapsulation. Unencapsulated vinorelbine was removed by gel-chromatography as above. Typically >80% of the drug remained encapsulated into so obtained Ni-NTA-PEG-DSPE-containing liposomes. Control liposomes were made substituting PEG-DSPE for Ni-NTA-PEG-DSPE, and were loaded with vinorelbine in a similar way. Liposomes containing covalently bound 4G7 were prepared by incubating vinorelbine-loaded control liposomes with 4G7 conjugated to an amphipathic linker, maleimido-PEG-DSPE (Papahadjopoulos, et al. U.S. Pat. No. 6,210,707). Bovine endothelial cells (BEND-3) expressing vascular endothelial growth factor (VEGF) receptor were incubated (37° C., 6 hours) in the growth medium containing 0.03–90 microgram/mL of the free (i.e. non-encapsulated) vinorelbine, or vinorelbine encapsulated in the Ni-NTA-PEG-DSPE liposomes with or without 0.02 mg/niL of the internalizing anti-VEGER scFv antibody 4G7 having a hexahistidine tag and a terminal cysteine group. The cells were post-incubated in the growth medium without the drug for another 72 hours, and the viability of the cells was determined by a conventional tetrasolium (MTT) assay. The median cytotoxic dose, i.e. the dose that reduces the cell viability to 50% of non-treated control ($IC_{50}$), was as follows: free vinorelbine, 0.67 µg/mL; vinorelbine in Ni-NTA-PEG-DSPE liposomes without 4G7 scFv, >100 µg/mL ($IC_{50}$ not reached); control liposomes+4G7 scFv, >100 µg/mL ($IC_{50}$ not reached); vinorelbine in liposomes with covalently bound 4G7, 2.5 µg/ml; Ni-NTA-PEG-DSPE liposomes+4G7 scFv, 1.4 µg/mL. Thus, we observed specific delivery of vinorelbine into vascular epithelial cells by Ni-NTA-PEG-DSPE-containing liposomes coupled to a receptor-specific scFv via a hexahistidine tag.

Example 4

Targeted Delivery of Methotrexate into Cancer Cells by Ni-NTA-PEG-DSPE Liposomes and a Hexahistidine-talged Antibody Liposomes containing methotrexate were made from DSPC, cholesterol, and PEG(2000)-DSPE (molar ratio, 3:2: 0.025) and 100 mg/mL solution of methotrexate sodium in 10 mM buffer solution of N-4-hydroxyethyl-piperazino-ethylsulfonic acid (HEPES) sodium salt, pH 7.2, by a reverse phase evaporation method of Szoka and Papahadjopoulos (*Proc. Natl. Acad. Sci. USA*, 75:4134–4178, 1978). Unencapsulated methotrexate was separated by gel-chromatography using 20 mM HEPES, 144 mM NaCl (HBS buffer) as eluate. Resulting liposomes containing 150±7 mg methotrexate per mrol of liposomal phospholipid, were incubated (55° C., 30 min) with Ni-NTA-PEG-DSPE, dissolved in HBS buffer, in the amount of 2 mol. % of the liposomal phospholipid. No drug leakage from the liposomes was detected during this incubation. Median cytotoxic dose ($IC_{50}$) of these liposomes, with or without 4G7 scFv, as well as of the free methotrexate, was determined in the culture of BEND3 cells as described in the Example 3, to be as follows: free methotrexate, >90 µg/ml (not reached); methotrexate in Ni-NTA-PEG-DSPE-liposomes without antibody, >90 µg/ml (not reached); methotrexate in Ni-NTA-PEG-DSPE-liposomes in the presence of hexahistidine-tagged 4G7 scFv, 9 µg/ml. Thus, incorporation of Ni-NTA-PEG-DSPE into pre-formed methotrexate liposomes produced a methotrexate-carrying liposome that formed an internalizable construct with a His-tagged antibody.

Example 5

Loading of Cytotoxic Drugs into Liposomes Containing Various Ni-NTA Lipids

The nature of Ni-NTA lipid in the liposomes had an unexpected effect on the efficiency of cytotoxin encapsulation by a transmembrane gradient method. Liposomes with entrapped 0.25 M ammonium sulfate were prepared using the lipid matrix composed of DSPC, cholesterol (Chol), and PEG-DSPE in the molar ratio 3:2:0.03 (Preparation A), DSPC, Chol, PEG-DSPE, and Ni-NTA-DOGS in the molar ratio 3:2:0.03:0.06 (Preparation B), and DSPC, Chol, and Ni-NTA-PEG-DSPE (compound V) in the molar ratio 3:2: 0.03:0.06 (Preparation C). After bringing the liposomes into 5% dextrose, % M MES-Na buffer pH 5.5 (MES-Dextrose), the liposomes were incubated (55° C., 30 min) with vinorelbine (VNR) or doxorubicin (DOX) at the input drug/lipid ratio of 150 mg of the drug per mmol of the liposome phospholipid. The liposome were chilled in ice, and separated from unencapsulated drug by gel-chromatography using MES-Dextrose buffer. The concentration of liposome phospholipid was determined spectrophotometrically by the molybdate-ascorbic acid method following acid digestion of the liposomes. The concentration of the liposome drug was determined spectrophotometrically after solubilization of the liposomes in 80% aqueous methanol (vinorelbine, absorbance at 370 nm), or 70% aqueous isopropanol-0.1M HCl (doxorubicine, absorbance at 485 nm) by comparison to standard curves. The loading efficiency was calculated as percent encapsulated drug of total added for loading. The results are shown in Table 1.

TABLE 1

Results for drug loading in liposomes.

| Preparation | Drug | Drug loading, mg/mmol of phospholipid | Loading efficiency, % |
|---|---|---|---|
| DSPC/Chol/PEG-DSPE (A) | VNR | 150.2 ± 4.9 | 100.2 ± 3.4 |
| DSPC/Chol/PEG-DSPE/Ni-NTA-DOGS (B) | VNR | 13.6 ± 1.2 | 9. ± 0.9 |
| DSPC/Chol/PEG-DSPE/Ni-NTA-PEG-DSPE (C) | VNR | 149.6 ± 5.8 | 99.8 ± 4.0 |
| DSPC/Chol/PEG-DSPE (A) | DOX | 159.4 ± 6.1 | 106.3 ± 14.4 |
| DSPC/Chol/PEG-DSPE/Ni-NTA-DOGS (B) | DOX | 40.4 ± 4.3 | 26.9 ± 3.0 |
| DSPC/Chol/PEG-DSPE/Ni-NTA-PEG-DSPE (C) | DOX | 138.2 ± 10.2 | 92.2 ± 8.0 |

The nature of Ni-NTA-lipid had little effect on the encapsulation by direct sequestration of the lipid hydration medium (HPTS, MTX), such as reverse phase evaporation. Direct sequestration, however, is inefficient (MTX loading efficiency 28.7–29.5%), compared to gradient methods that provide almost quantitative encapsulation. Thus, unexpectedly, only the polymer-linked NTA lipid provided for the efficient loading of the drugs by an advantageous, transmembrane-gradient-based method.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting ligand internalization into a cell, said method comprising:
   i) contacting said cell with a ligand and a reporter, wherein the reporter non-covalently couples to the ligand;
   ii) dissociating the reporter from non-internalized ligand bound to a surface of said cell and removing dissociated reporter from the surface of said cell while said non-internalized ligand remains bound to the cell surface; and
   iii) detecting the presence of the reporter remaining in said cell, whereby the presence of the reporter indicates that said ligand is internalized into said cell.

2. The method of claim 1, wherein contacting the cell with the ligand and the reporter comprises:
   contacting said cell with a ligand comprising an epitope tag; and
   contacting the ligand with a reporter comprising a moiety that binds said epitope tag.

3. The method of claim 1, wherein said ligand is a ligand that binds to a cell surface receptor.

4. The method of claim 1, wherein said ligand is a peptide.

5. The method of claim 1, wherein said ligand is selected from the group consisting of an antibody, scFv, Fv, Fab, a monoclonal antibody, a cytokine, and a growth factor.

6. The method of claim 1, wherein said ligand is a member of a combinatorial library.

7. The method of claim 6, wherein said combinatorial library comprises a combinatorial chemical library, a recombinant library, or a phage display library.

8. The method of claim 1, wherein said reporter is non-covalently coupled to the ligand via an epitope tag.

9. The method of claim 8, wherein the epitope tag is selected from the group consisting of a Ths-tag, a Flag-tag, an HA-tag, a myc-tag, and a DYKDDDDK epitope.

10. The method of claim 1, wherein the reporter is selected from the group consisting of an enzyme, a colorimetric label, a fluorescent label, a luminescent label, a radioactive label, a nanoparticle, a spin label, a magnetic bead, and a liposome.

11. The method of claim 8, wherein said epitope tag is a hexahistidine (His-6) tag and said reporter is a liposome comprising a nitrilotriacetic acid (NTA) lipid or an iminodiacetic acid (IDA) lipid.

12. The method of claim 8, wherein said ligand is an antibody and said epitope tag is attached to said antibody through a covalent linkage to protein A or protein G.

13. The method of claim 1, wherein said cell is a cancer cell.

14. The method of claim 1, further comprising:
   iv) identifying the ligand that is internalized into said cell.

15. The method of claim 14, wherein identifying the ligand comprises determining the amino acid sequence of the internalized ligand or determining the sequence of a nucleic acid encoding said ligand.

16. The method of claim 8, wherein the epitope tag comprises a polyhistidine tag, and wherein the noncovalent bond comprises a metal chelation band between the reporter and the polyhistidine tag.

17. The method of claim 16, wherein the reporter is selected from the group consisting of an enzyme, a colorimetric label, a fluorescent label, a luminescent label, a radioactive label, a nanoparticle, a spin label, a magnetic bead, and a liposome.

18. The method of claim 16, wherein the reporter comprises a metal ion cornplexed to a chelator selected from the group consisting of NTA, IDA, a C-substituted derivative of NTA, and a C-substituted derivative of IDA.

19. The method of claim 18, wherein the metal ion comprises a divalent ion of Cu, Ni, Co or Zn.

20. The method of claim 2, wherein the ligand and the reporter are combined to Loin a non-covalent bond prior to the contacting step.

21. The method of claim 2, wherein the ligand and the reporter are combined to form a non-covalent bond during the contacting step.

22. The method of claim 1, wherein the method is performed in a microtiter plate.

23. The method of claim 1, wherein detecting the presence of the reporter comprises performing scintillography or autoradiagraphy.

24. The method of claim 1, wherein detecting the presence of the reporter comprises performing fluorimetry, flow cytometry or fluorescent microscopy.

25. The method of claim 1, wherein detecting the presence of the reporter comprises determining cell proliferation or cell mortality.

26. The method of claim 1, wherein detecting the presence of the reporter comprises isolating the cell comprising the internalized ligand.

27. The method of claim 1, wherein detecting the presence of the reporter comprises a quantitative determination.

28. The method of claim 1, wherein detecting the presence of the reporter comprises:
   a) performing a first detecting step prior to dissociating reporter from the non-internalized ligand and,
   b) performing a second detecting step after dissociating reporter from the non-internalized ligand.

29. The method of claim 1, wherein contacting the cell with the ligand and the reporter comprises contacting the cell with at least two different ligands.

30. The method of claim 1, wherein steps i, ii and iii are performed on a plurality of cells.

31. The method of claim 30, wherein detecting the presence of the reporter comprises detecting one or more cells comprising the reporter.

32. The method of claim 31, wherein the reporter comprises a fluorescent label, and wherein the one or more cells are detected by flow cytometry, fluorescent microscopy, or fluorescence-activated cell sorting.

33. The method of claim 31, wherein the reporter comprises a magnetic bead, and wherein the one or more cells are detected by magnetometry or by magnetic separation.

34. The method of claim 31, wherein the reporter comprises a radioactive label, and wherein the one or more cells are detected by autoradiography.

35. The method of claim 30, further comprising isolating, from the plurality of cells, a cell that internalized the ligand.

36. The method of claim 30, wherein detecting the presence of the reporter comprises quantification of the reporter present in a member cell of the plurality of cells.

* * * * *